United States Patent
Gazit et al.

(10) Patent No.: US 11,547,348 B2
(45) Date of Patent: Jan. 10, 2023

(54) NON-INVASIVE PH-DEPENDENT IMAGING USING QUANTITATIVE CHEMICAL EXCHANGE SATURATION TRANSFER (QCEST)

(71) Applicant: Cedars-Sinai Medical Center, Los Angeles, CA (US)

(72) Inventors: Dan Gazit, Los Angeles, CA (US); Debiao Li, South Pasadena, CA (US); Gadi Pelled, Los Angeles, CA (US); Zulma Gazit, Los Angeles, CA (US); Zhengwei Zhou, Sherman Oaks, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 1001 days.

(21) Appl. No.: 16/305,221

(22) PCT Filed: Jun. 8, 2017

(86) PCT No.: PCT/US2017/036617
§ 371 (c)(1),
(2) Date: Nov. 28, 2018

(87) PCT Pub. No.: WO2017/214439
PCT Pub. Date: Dec. 14, 2017

(65) Prior Publication Data
US 2020/0315522 A1    Oct. 8, 2020

Related U.S. Application Data

(60) Provisional application No. 62/347,509, filed on Jun. 8, 2016.

(51) Int. Cl.
*A61B 5/055*    (2006.01)
*A61B 5/145*    (2006.01)
(Continued)

(52) U.S. Cl.
CPC ............ *A61B 5/4566* (2013.01); *A61B 5/055* (2013.01); *A61B 5/14539* (2013.01);
(Continued)

(58) Field of Classification Search
CPC ... A61B 5/4566; A61B 5/055; A61B 5/14539; A61B 5/4824; A61B 5/7275;
(Continued)

(56) References Cited

U.S. PATENT DOCUMENTS 10,638,948 B2    5/2020 Gazit et al.
2011/0054299 A1    3/2011 Ling et al.
(Continued)

FOREIGN PATENT DOCUMENTS

EP    2986210 A1    2/2016
EP    2986210 B1    3/2019
(Continued)

OTHER PUBLICATIONS

Kim et al., Assessment of glycosaminoglycan distribution in human lumbar intervertebral discs using chemical exchange saturation transfer, Proceedings of the International Society for Magnetic Resonance in Medicine, 2010, vol. 18, p. 539.
(Continued)

*Primary Examiner* — Daniel L Cerioni
*Assistant Examiner* — Alyssa N Potter
(74) *Attorney, Agent, or Firm* — Nixon Peabody LLP

(57) ABSTRACT

In various embodiments, the invention teaches systems and methods for magnetic resonance imaging. In some embodiments, the invention teaches systems and methods for determining the source of pain in intervertebral discs by measuring one or more physiological biomarkers associated with disc pain and/or disc degeneration.

24 Claims, 18 Drawing Sheets

(51) Int. Cl.
  *G01R 33/483* (2006.01)
  *G01R 33/56* (2006.01)
  *A61B 5/00* (2006.01)
(52) U.S. Cl.
  CPC .......... *A61B 5/4824* (2013.01); *A61B 5/7275* (2013.01); *G01R 33/4838* (2013.01); *G01R 33/5605* (2013.01)
(58) Field of Classification Search
  CPC .... A61B 5/407; A61B 5/004; G01R 33/4838; G01R 33/5605
  See application file for complete search history.

(56) References Cited

U.S. PATENT DOCUMENTS

| | | |
|---|---|---|
| 2011/0087087 A1 | 4/2011 | Peacock et al. |
| 2014/0316246 A1 | 10/2014 | Gounis |
| 2015/0323632 A1 | 11/2015 | Sun |
| 2016/0081578 A1 | 3/2016 | Gazit et al. |
| 2016/0082132 A1 | 3/2016 | Yang et al. |
| 2016/0136310 A1 | 5/2016 | Bradford et al. |

FOREIGN PATENT DOCUMENTS

| | | |
|---|---|---|
| JP | 2007-152128 A | 6/2007 |
| JP | 2009-508970 A | 3/2009 |
| JP | 2015-144825 A | 8/2015 |
| WO | 2007/035906 A2 | 3/2007 |
| WO | WO 2014/172682 A1 | 10/2014 |
| WO | WO 2017/214439 A1 | 12/2017 |

OTHER PUBLICATIONS

Kim et al., Assessment of Glycosaminoglycan Distribution in Human Lumbar Intervertebral Discs Using Chemical Exchange Saturation Transfer at 3 T: Feasibility and Initial Experience, NMR Biomed, 2011, vol. 24(9), pp. 1137-1144.
International Search Report and Written Opinion for PCT/US2014/034720 dated Sep. 23, 2014, 9 pages.
International Preliminary Report on Patentability for PCT/US2014/034720 dated Oct. 20, 2015, 8 pages.
EP 14786020.9 Extended European Search Report dated Sep. 20, 2016, 6 pages.
International Search Report and Written Opinion for PCT/US2017/036617 dated Aug. 29, 2017, 12 pages.
An et al., Introduction: Disc Degeneration: Summary, Spine, 2004, vol. 29, pp. 2677-2678.
Anderson et al., Variation in the COMT gene: implications for pain perception and pain treatment. Pharmacogenomics, 2009, vol. 10, 669-684.
Andersson, G. B., Epidemiological features of chronic low-back pain. Lancet, 1999, vol. 354, pp. 581-585.
Antoniou et al., Quantitative Magnetic Resonance Imaging in the Assessment of Degenerative Disc Disease, Magnetic Resonance in Medicine, 1998, vol. 40, pp. 900-907.
Asicioglu et al., Maternal and perinatal outcomes of eclampsia with and without HELLP syndrome in a teaching hospital in western Turkey, J. Obstet. Gynaecol., 2014, vol. 34, pp. 326-331.
Auerbach et al., In vivo quantification of human lumbar disc degeneration using T(1rho)-weighted magnetic resonance imaging, Eur. Spine J., 2006, vol. 15, Suppl. 3, pp. S338-S344.
Blumenkrants et al., In Vivo 3.0-Tesla Magnetic Resonance Tip and T2 Relaxation Mapping in Subjects with Intervertebral Disc Degeneration and Clinical Symptoms, Magn. Reson. Med., 2010, vol. 63(5), pp. 1193-1200.
Boos et al., Tissue characterization of symptomatic and asymptomatic disc herniations by quantitative magnetic resonance imaging, J. Orthop. Res., 1997, vol. 15, pp. 141-149.
Borenstein et al., The Value of Magnetic Resonance Imaging of the Lumbar Spine to Predict Low-Back Pain in Asymptomatic Subjects : A Seven-Year Follow-Up Study, Journal of Bone and Joint Surgery, 2001, vol. 83A(9), pp. 1306-1311.
Borthakur et al., T1rho magnetic resonance imaging and discography pressure as novel biomarkers for disc degeneration and low back pain, Spine (Phila Pa 1976), 2011, vol. 36, pp. 2190-2196.
Carragee et al., Does Discography Cause Accelerated Progression of Degeneration Changes in the Lumbar Disc: A Ten-Year Matched Cohort Study, Spine, 2009, vol. 34, pp. 2338-2345.
Chatani et al., Topographic differences of 1H-NMR relaxation times (T1, T2) in the normal intervertebral disc and its relationship to water content, Spine (Phila Pa 1976), 1993, vol. 18, pp. 2271-2275.
Chen et al., Quantitative T(1)(rho) Imaging using Phase Cycling for B0 and B1 Field Inhomogeneity Composition, Magn Reson Imaging, 2011, vol. 29, pp. 608-619.
Chiu et al., Magnetic resonance imaging measurement of relaxation and water diffusion in the human lumbar intervertebral disc under compression in vitro, Spine (Phila Pa 1976), 2001, vol. 26, pp. E437-E444.
Coppes et al., Innervation of annulus fibrosis in low back pain, Lancet, 1990, vol. 336, pp. 189-190.
Cuesta et al., Acid-sensing ion channels in healthy and degenerated human intervertebral disc, Connect Tissue Res., 2014, vol. 55, pp. 197-204.
Dixon et al., A Concentration-Independent Method to Measure Exchange Rates in PARACEST Agents, Magnetic Resonance in Medicine, 2010, vol. 63, pp. 625-632.
Donnerer et al., Increased content and transport of substance p. and calcitonin gene-related peptide in sensory nerves innervating inflamed tissue: evidence for a regulatory function of nerve growth factor in vivo. Neuroscience, 1992, vol. 49, pp. 693-698.
Dray et al., Bradykinin and inflammatory pain. Trends Neurosci., 1993, vol. 16, pp. 99-104.
Englander et al., Hydrogen Exchange, Annu. Rev. Biochem., 1972, vol. 41, pp. 903-924.
Freemont et al., Nerve ingrowth into diseased intervertebral disc in chronic back pain, Lancet, 1997, vol. 350, pp. 178-181.
Gilbert et al., Acidic pH promotes intervertebral disc degeneration: Acid-sensing ion channel-3 as a potential therapeutic target, Sci. Rep., 2016, vol. 6, 37360, pp. 1-12.
Gruber et al., Genome-wide analysis of pain-, nerve- and neurotrophin-related gene expression in the degenerating human annulus. Mol. Pain, 2012, vol. 8 (63), pp. 1-18.
Haneder et al., Assessment of Glycosaminoglycan Content in Intervertebral Discs using Chemical Exchange Saturation Transfer at 3.0 Tesla: Preliminary Results in Patients with Low-Back Pain, Eur Radiol, 2013, vol. 23, pp. 861-868.
Haris et al., Exchange rates of creatine kinase metabolites: feasibility of imaging creatine by chemical exchange saturation transfer MRI. NMR Biomed., 2012, vol. 25, pp. 1305-1309.
Heo et al., Accelerating Chemical Exchange Saturation Transfer (CEST) MRI by Combining Compressed Sensing and Sensitivity Encoding Techniques, Magnetic Resonance in Medicine, 2017, vol. 77(2), pp. 779-786.
Ichimura et al., Cell culture of the intervertebral disc of rats: factors influencing culture, proteoglycan, collagen, and deoxyribonucleic acid synthesis, J. Spinal Disord. 1991, vol. 4, pp. 428-436.
Jin et al., Spin-Locking vs. Chemical Exchange Saturation Transfer MRI for Investigating Chemical Exchange Process Between Water and Labile Metabolite Protons, Magnetic Resonance in Medicine, 2011, vol. 65(5), pp. 1448-1460.
Jin et al., Magnetic Resonance Imaging of the Amine-Proton Exchange (APEX) Dependent Contrast, Neuroimage, 2012, vol. 59(2), pp. 1218-1227.
Johannessen et al., Assessment of Human Disc Degeneration and Proteoglycan Content Using T1ρ-weighted Magnetic Resonance Imaging, Spine, 2006, vol. 31(11), pp. 1253-1257.
Kang et al., Can magnetic resonance imaging accurately predict concordant pain provocation during provocative disc injection? Skeletal Radiol., 2009, vol. 38, pp. 877-885.
Keshari et al., Lactic Acid and Proteoglycans as Metabolic Markers for Discogenic Back Pain, Spine, 2008, vol. 33, pp. 312-317.

(56) References Cited

OTHER PUBLICATIONS

Kim et al., Disc Degeneration in the Rabbit: A Biochemical and Radiological Comparison Between Four Disc Injury Models, Spine, 2004, vol. 30, pp. 33-37.

Kim et al., Water Saturation Shift Referencing (WASSR) for Chemical Exchange Saturation Transfer Experiments, Magnetic Resonance in Medicine, 2009, vol. 61(6), pp. 1441-1450.

Kim et al., Assessment of Glycosaminoglycan Distibution in Human Lumbar Intervertebral Discs Using Chemical Exchange Saturation Transfer at 3 T: Feasibility and Initial Experience, NMR Biomed, 2010, vol. 24(9), pp. 1137-1144.

Kim et al., A review of optimization and quantification techniques for chemical exchange saturation transfer MRI toward sensitive in vivo imaging, Contrast Media Mol. Imaging, 2015, vol. 10, pp. 163-178.

Knox et al., The Incidence of Low Back Pain in Active Duty United States Military Service Members, Spine, 2011, vol. 36, pp. 1492-1500.

Lee et al., In Vitro Study of Endogenous CEST Agents at 3 T and 7 T, Contrast Media Mol Imaging, 2016, vol. 11, pp. 4-14.

Lefevre-Colau et al., Frequency and interrelations of risk factors for chronic low back pain in a primary care setting, PLoS One, 2009, vol. 4, e4874, pp. 1-7.

Li et al., Chemical Exchange Saturation Transfer and R1RHO Dispersions of Polypeptides with Varying Complexities, Proc. Intl. Soc. Magnetic Resonance in Medicine, 2011, vol. 19, p. 4495.

Li et al., Simultaneous Acquisition of T1ρ and T2 Quantification in Knee Cartilage: Reproducibility and Diurnal Variation, Magn Reson Imaging, 2014, vol. 39(5), pp. 1287-1293.

Liang et al., The Relationship Between Low pH in Intervertebral Discs and Low Back Pain: A Systematic Review, Arch Med Sci, 2012, vol. 8, pp. 952-956.

Liang et al., New Hypothesis of Chronic Back Pain: Low pH Promotes Nerve Ingrowth into Damaged Intervertebral Disks, Acta Anaesthesiol Scand, 2013, vol. 57, pp. 271-277.

Ling et al., Assessment of Glycosaminoglycan Concentration In Vivo by Chemical Exchange-Dependent Saturation Transfer (gagCEST), PNAS, 2008, vol. 105, pp. 2266-2270.

Liu et al., Reliable Chemical Exchange Saturation Transfer Imaging of Human Lumbar Intervertebral Discs Using Reduced-Field-of-View Turbo Spin Echo at 3.0 T, NMR in Biomedicine, 2013, vol. 26, pp. 1672-1679.

Liu et al., Chemical Exchange and In Vivo Intervertebral Disc R1-RHO Dispersion Imaging: A Feasibility Study, ISMRM 21st Annual Meeting and Exhibition, 2013, vol. 3, p. 2403.

Liu et al., Detection of Low Back Pain using pH Level-Dependent Imaging of the Intervertebral Disc using the Ratio of R1ρ Dispersion and -OH Chemical Exchange Saturation Transfer (RROC), Magnetic Resonance in Medicine, 2015, vol. 73, pp. 1196-1205.

Liu et al., Biological behavior of human nucleus pulposus mesenchymal stem cells in response to changes in the acidic environment during intervertebral disc degeneration, Stem Cells Dev., 2017, vol. 26(12), pp. 901-911.

Majumdar et al., Diagnostic tools and imaging methods in intervertebral disk degeneration. Orthop Clin North Am., 2011, vol. 42, pp. 501-511.

Meissner et al., Quantitative pulsed CEST-MRI using Ω-plots, NMR in Biomedicine, 2015, vol. 28, pp. 1196-1208.

Melkus et al., Ex Vivo Porcine Model to Measure pH Dependence of Chemical Echange Saturation Transfer Effect of Glycosaminoglycan in the Intervertebral Disc, Magnetic Resonance in Medicine, 2014, vol. 71, pp. 1743-1749.

Menkin, V., Biochemical Mechanisms in Inflammation, Br. Med. J., 1960, vol. 1, pp. 1521-1528.

Mizrahi et al., Nucleus pulposus degeneration alters properties of resident progenitor cells, Spine, 2013, J12, pp. 803-814.

Muller-Lutz et al., Gender, BMI and T2 Dependencies of Glycosaminoglycan Chemical Exchange Saturation Transfer in Intervertebral Discs, Magn Reson Imaging, 2016, vol. 34, pp. 271-275.

Nachemson et al., Intradiscal Measurements of pH in Patients with Lumbar Rhizopathies, Acta Orthopaedica Scandinavica, 1969, vol. 40, pp. 23-42.

Navone et al., Expression of neural and neurotrophic markers in nucleus pulposus cells isolated from degenerated intervertebral disc, J. Orthop. Res., 2012, vol. 30, 1470-1477.

Ohtori et al., Up-regulation of acid-sensing ion channel 3 in dorsal root ganglion neurons following application of nucleus pulposus on nerve root in rats, Spine (Phila Pa 1976), 2006, vol. 31, pp. 2048-2052.

Orita et al., Inhibiting nerve growth factor or its receptors downregulates calcitonin gene-related peptide expression in rat lumbar dorsal root ganglia innervating injured intervertebral discs. J. Orthop. Res., 2010, vol. 28, pp. 1614-1620.

Osti et al., MRI and Discography of Annular Tears and Intervertebral Disc Degeneration, Journal of Bone and Joint Surgery, 1992, vol. 74B(3), pp. 431-435.

Peng et al., The pathogenesis of discogenic low back pain, J. Bone Joint Surg. Br., 2005, vol. 87, pp. 62-67.

Purmessur et al., Expression and regulation of neurotrophins in the nondegenerate and degenerate human intervertebral disc, Arthritis Res. Ther., 2008, vol. 10, R99, p. 1-9.

Raj, P. P., Intervertebral disc: anatomy-physiology-pathophysiology-treatment, Pain Pract., 2008, vol. 8, pp. 18-44.

Recuerda et al., Assessment of Mechanical Properties of Isolated Bovine Intervertebral Discs from Multi-Parametric Magnetic Resonance Imaging, BMC Musculoskeletal Disorders, 2012, vol. 13, 14 pages.

Richardson et al., Degenerate human nucleus pulposus cells promote neurite outgrowth in neural cells, PLoS One 7, 2012, e47735, pp. 1-8.

Saar et al., Assessment of Glycosaminoglycan Concentration Changes in the Intervertebral Disc via Chemical Exchange Saturation Transfer, NMR in Biomedicine, 2012, vol. 25, pp. 255-261.

Schleich et al., Glycosaminoglycan Chemical Exchange Saturation Transfer of Lumbar Intervertebral Discs in Patients with Spondyloarthritis, Journal of Magnetic Resonance Imaging, 2015, vol. 42, pp. 1057-1063.

Sheyn et al., PTH promotes allograft integration in a calvarial bone defect, Mol. Pharm. 2013, vol. 10, pp. 4462-4471.

Sun et al., Detection of the ischemic penumbra using pH-weighted MRI, J. Cereb. Blood Flow Metab., 2007, vol. 27, pp. 1129-1136.

Sun et al., Relaxation-compensated fast multislice amide proton transfer (APT) imaging of acute ischemic stroke, Magn. Reson. Med., 2008, vol. 59, pp. 1175-1182.

Sun et al., Simplified and Scalable Numerical Solution for Describing Multi-Pool Chemical Exchange Saturation Transfer (CEST) MRI Contrast, J. Magn Reson., 2010, vol. 205(2), pp. 235-241.

Sun et al., Quantitative Chemical Exchange Saturation Transfer (qCEST) MRI—RF Spillover Effect-Corrected Omega Plot for Simultaneous Determination of Labile Proton Fraction Ratio and Exchange rate, Contrast Media Mol Imaging, 2014, vol. 9, pp. 268-275.

Sun et al., A Method for Accurate pH Mapping with Chemical Exchange Saturation Transfer (CEST) MRI, Contrast Media Mol Imaging, 2016, vol. 11(3), pp. 195-202.

Takashima et al., Correlation Between T2 Relaxation Time and Intervertebral Disk Degeneration, Skeletal Radiol, 2012, vol. 41, pp. 163-167.

Trattnig et al., Lumbar intervertebral disc abnormalities: comparison of quantitative T2 mapping with conventional MR at 3.0 T, Eur. Radiol., 2010, vol. 20, pp. 2715-2722.

Uchiyama et al., Expression of acid-sensing ion channel 3 (ASIC3) in nucleus pulposus cells of the intervertebral disc is regulated by p75NTR and ERK signaling. J. Bone Miner. Res., 2007, vol. 22, pp. 1996-2006.

Urban et al., Swelling pressure of the inervertebral disc: influence of proteoglycan and collagen contents, Biorheology, 1985, vol. 22, pp. 145-157.

Urban et al., Nutrition of the intervertebral disc, Spine, 2004, vol. 29, pp. 2700-2709.

(56) References Cited

OTHER PUBLICATIONS

Van Zijl et al., Chemical Exchange Saturation Transfer (CEST): What is in a nName and What Isn't?, Magnetic Resonance in Medicine, 2011, vol. 65, pp. 927-948.

Vinogradov et al., CEST: from basic principles to applications, challenges and opportunities, J. Magn. Reson., 2013, vol. 229, pp. 155-172.

Wada et al., Glycosaminoglycan chemical exchange saturation transfer in human lumbar intervertebral discs: Effect of saturation pulse and relationship with low back pain, J. Magn. Reson. Imaging., 2017, vol. 45, pp. 863-871.

Wang et al., T1rho and T2 Relaxation Times for Lumbar Disc Degeneration: An In Vivo Comparative Study at 3.0-Tesla MRI, Eur Radiol, 2013, vol. 23, pp. 228-234.

Ward et al., A New Class of Contrast Agents for MRI Based on Proton Chemical Exchange Dependent Saturation Transfer (CEST), Journal of Magnetic Resonance, 2000, vol. 143, pp. 79-87.

Watanabe et al., Relationship between immuno staining intensity and antigen content in sections, J. Histochem. Cytochem., 1996, vol. 44, pp. 1451-1458.

Wu et al., Quantitative Chemical Exchange Saturation Transfer (qCEST) MRI—Omega Plot Analysis of RF-Spillover-Corrected Inverse CEST Ratio Asymmetry for Simultaneous Determination of Labile Proton Ratio and Exchange Rate, NMR in Biomedicine, 2015, vol. 28, pp. 376-383.

Wu et al., Quantitative Description of Radiofrequency (RF) Power-Based Ratiometric Chemical Exchange Saturation Transfer (CEST) pH Imaging, NMR in Biomedicine, 2015, vol. 28, pp. 555-565.

Zaiss et al., Quantitative Separation of CEST Effect from Magnetization Transfer and Spillover Effects by Lorentzian-Line-Fit Analysis of Z-Spectra, J. Magn. Reson., 2011, vol. 211, pp. 149-155.

Zaiss et al., Inverse Z-Spectrum Analysis for Spillover-, MT-, and T1-Corrected Steady-State Pulsed CEST-MRI—Application to pH-Weighted MRI of Acute Stroke, NMR in Biomedicine, 2014, vol. 27, pp. 240-252.

Zhao et al., The cell biology of intervertebral disc aging and degeneration, Ageing Res. Rev., 2007, vol. 6, pp. 247-261.

Zhou et al., Using the amide proton signals of intracellular proteins and peptides to detect pH effects in MRI, Nat. Med. 2003, vol. 9, pp. 1085-1090.

Zhou et al., Defining an Acidosis-Based Ischemic Penumbra from pH-Weighted MRI, Transl. Stroke Res., 2011, vol. 3, pp. 76-83.

Zhou et al., Quantitative chemical exchange saturation transfer MRI of intervertebral disc in a porcine model. Magn. Reson. Med., 2016, vol. 76, pp. 1677-1683.

Zu et al., Optimizing Pulsed-Chemical Exchange Saturation Transfer (CEST) Imaging Sequences, Magn Reson Med., 2011, vol. 66(4), pp. 1100-1108.

Zuo et al., Assessment of Intervertebral Disc Degeneration with Magnetic Resonance Single-Voxel Spectroscopy, Magn. Reson Med, 2009, vol. 62(5), pp. 1140-1146.

Zuo et al., In Vivo Intervertebral Disc Characterization using Magnetic Resonance Spectroscopy and T1(rho) Imaging: Association with Discography and Oswestry Disability Index and SF-36, Spine (Phila Pa 1976), 2012, vol. 37(3), pp. 214-221.

International Preliminary Report on Patentability for PCT/US2017/036617 dated Dec. 20, 2018, 8 pages.

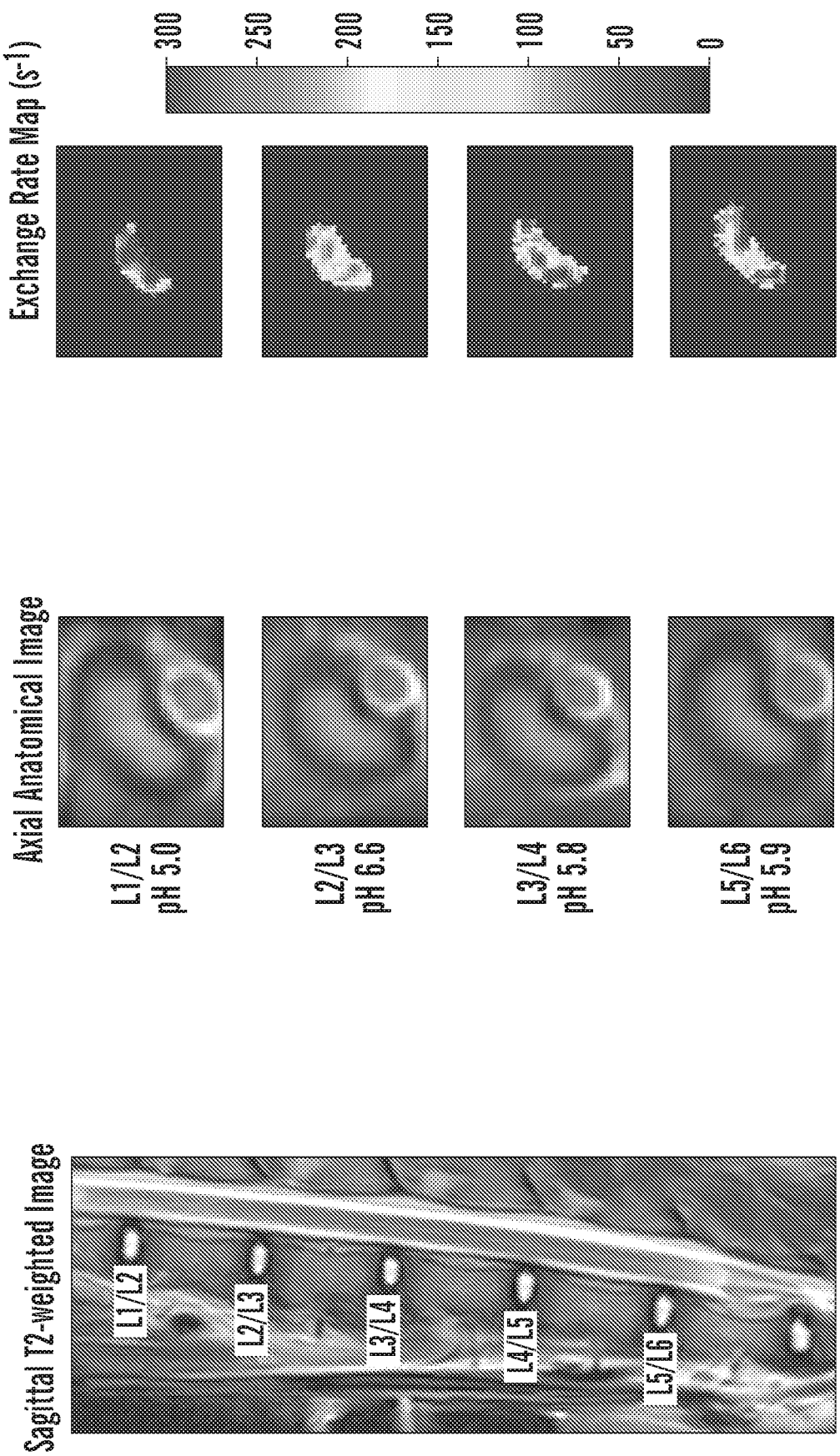

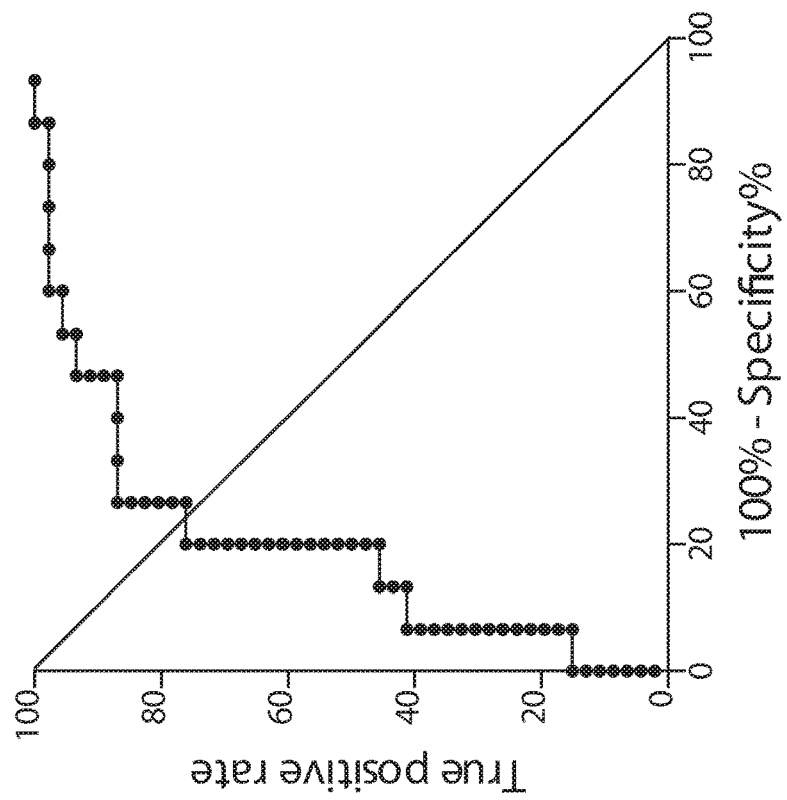
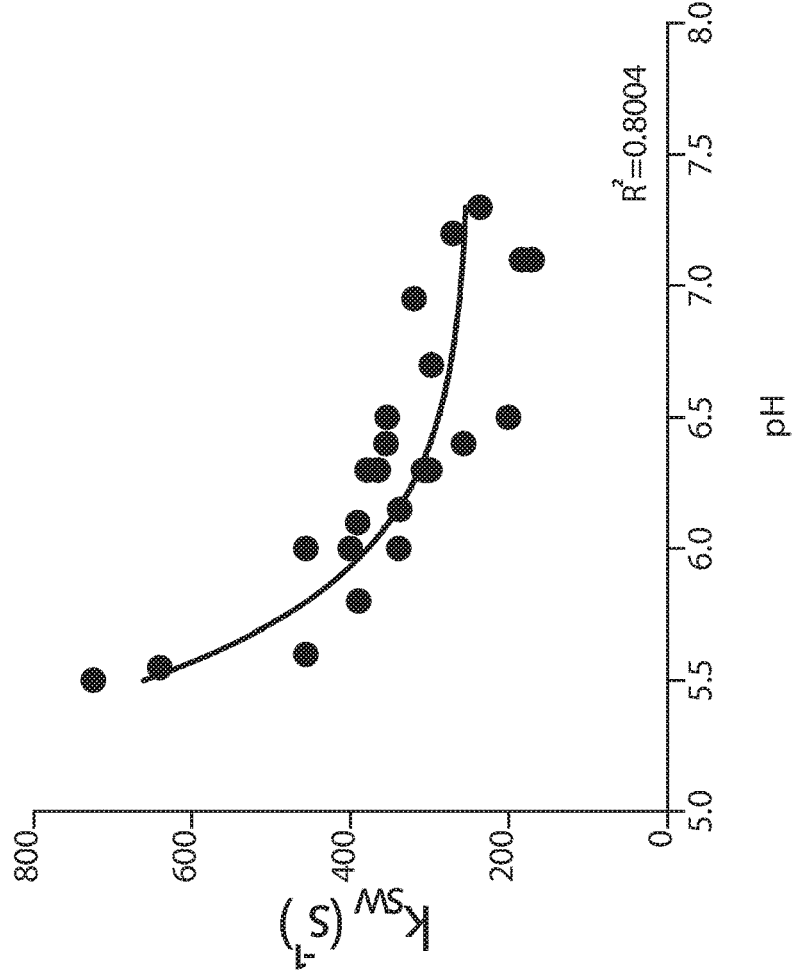
FIG. 8A
FIG. 8B

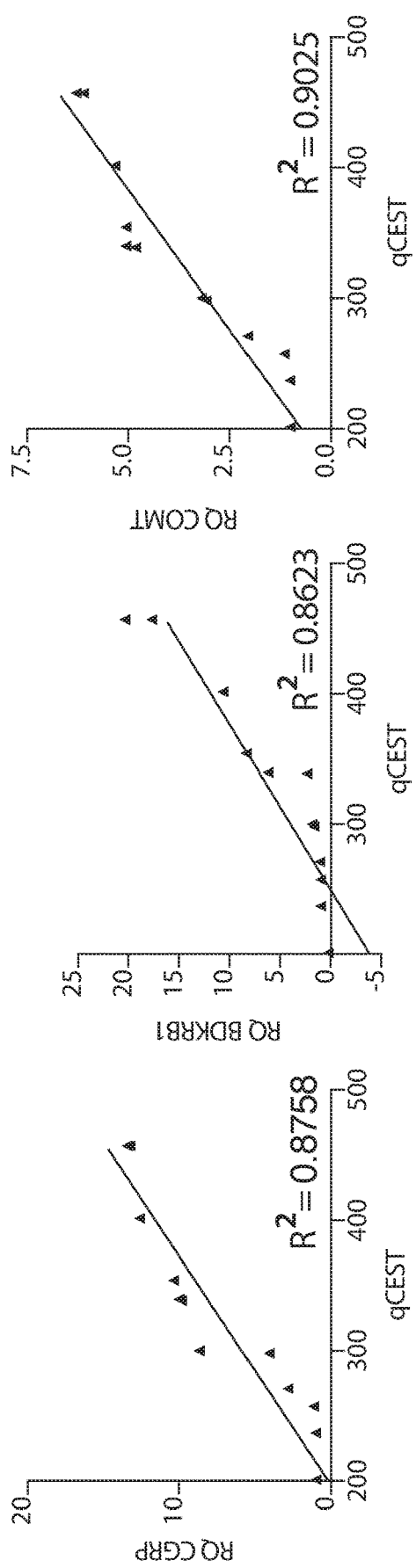
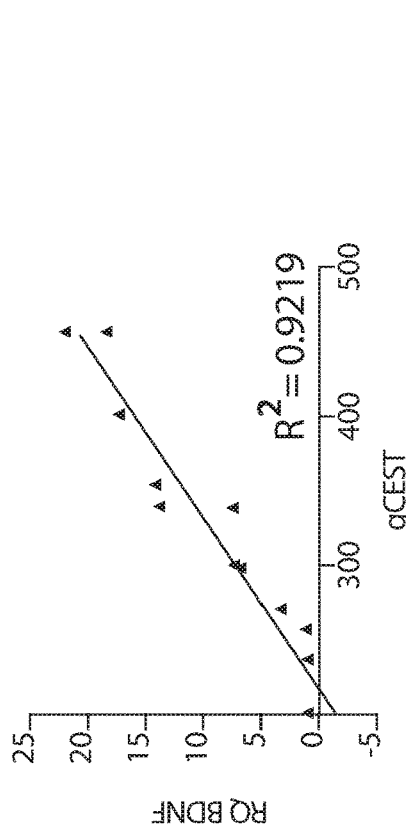
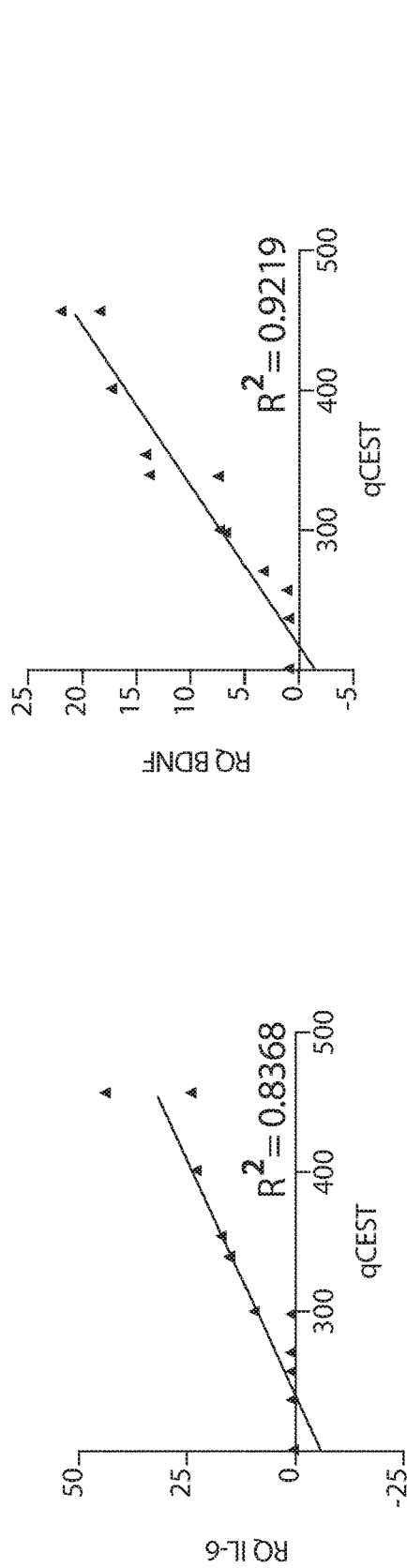
FIG. 11A  FIG. 11B  FIG. 11C  FIG. 11D  FIG. 11E

NON-INVASIVE PH-DEPENDENT IMAGING USING QUANTITATIVE CHEMICAL EXCHANGE SATURATION TRANSFER (QCEST)

CROSS-REFERENCE TO RELATED APPLICATIONS

This application is a National Phase of International Application No. PCT/US2017/036617 filed Jun. 8, 2017, which designated the U.S. and that International Application was published under PCT Article 21(2) in English, which also includes a claim of priority under 35 U.S.C. § 119(e) to U.S. Provisional Patent Application No. 62/347,509 filed Jun. 8, 2016, the contents of which are herein incorporated by reference in their entirety.

STATEMENT REGARDING FEDERALLY SPONSORED RESEARCH OR DEVELOPMENT

This invention was made with government support under Grant No. AR066517 awarded by National Institutes of Health. The government has certain rights in the invention.

FIELD OF THE INVENTION

The present invention generally relates to systems and methods for imaging and image processing.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Lower back pain is a major medical condition estimated to affect up to 85% of the US population. Intervertebral disc (IVD) degeneration is often associated with back pain. Although degenerate discs can be identified using magnetic resonance imaging (MRI), they do not always cause pain. Therefore, if a patient with lower back pain has several degenerate discs, further examination is required to determine which disc is the source of the pain, prior to a decision of surgical intervention. Standard procedures include discography, during which the suspected discs are pressurized in order to provoke pain. This is a painful procedure that is also known to further accelerate disc degeneration, disc herniation, and loss of disc height and affect the adjacent endplates. It is also subjective to variations of the placement of the needle, pressure exerted, and anesthesia. Recent studies have associated low pH with discogenic pain. It is believed that pH could potentially serve as a new metabolic biomarker for discogenic back pain.

Chemical exchange saturation transfer (CEST) is an emerging MR (magnetic resonance) technique to measure pH-dependent signal changes. This technique exploits the constant chemical exchange, which is pH-sensitive, between water protons and solute protons in certain molecules. The chemical exchange rate is dependent on pH values. The solute protons are first magnetization-saturated with a series of frequency selective radiofrequency (RF) pulses, and after exchanging with water protons, the saturation is indirectly detected in the water signal. For example, chemical exchange saturation transfer (CEST) is an emerging MR technique to detect glycosaminoglycan (GAG) content. This technique exploits the constant chemical exchange between the water protons and the hydroxyl protons in GAG. The hydroxyl protons will be first saturated, and after the transfer with water protons, the saturation will be indirectly detected in the water signal. Previous studies have applied gagCEST to explore the GAG content distribution in patients with degenerative disc disease. In addition to concentration, correlation with pH was also reported. However, the gagCEST contrast is a rather complicated effect. It involves multiple confounding factors, including but not limited to (a) exchange rate between water protons and GAG protons, which is dependent on the pH; (b) labile proton ratio, which is linearly correlated with GAG concentration; (c) water relaxation parameters $T_1$ and $T_2$; and (d) the RF irradiation power of CEST saturation module.

Recent studies have focused on separating the exchange rate or the labile proton ratio from other confounding factors in the CEST experiments. Among these methods, quantitative CEST (qCEST) allows for simultaneous measurements of the exchange rate and labile proton ratio. It was developed based on the observation that the CEST effect can be represented as a linear function of $1/B_1^2$. Multiple CEST experiments were performed with varying $B_1$ amplitudes for omega plot analysis.

Simultaneous measurements of pH value and concentration using qCEST have been shown in creatine phantom studies. Creatine protons have a slow to intermediate exchange rate with water protons. However, for GAG protons which undergo relatively faster chemical exchange, whether this technique can detect pH changes has not been investigated. In addition, most of the studies were performed on a preclinical scanner using continuous-wave (cw) saturation pulse. No in vivo validation has been performed and potential clinical application is not yet clear.

There is clearly a need in the art for improved systems and methods for diagnosing, prognosing, and monitoring the progression of conditions involving tissue degeneration, and particularly those associated with back pain.

SUMMARY OF THE INVENTION

The following embodiments and aspects thereof are described and illustrated in conjunction with systems, compositions, articles of manufacture, and methods which are meant to be exemplary and illustrative, not limiting in scope.

In various embodiments, the present invention provides a method for diagnosing a condition in a subject, the method comprising: imaging a region of a subject's body with a magnetic resonance imaging (MRI) scanner, wherein the region is imaged using a quantitative chemical exchange saturation transfer (qCEST) sequence; measuring one or more physiological biomarkers within the imaged region, wherein the physiological biomarkers comprise a labile proton exchange rate ($k_{sw}$) between a solute pool and a water pool; and determining that the subject has the condition if the labile proton exchange rate is increased relative to a reference value. In some embodiments, the increased labile proton exchange rate is correlated to a low pH value. In some embodiments, the increased labile proton exchange rate is greater than 200 exchanges/second. In some embodiments, the increased labile proton exchange rate is from 201 to 1000 exchanges/second. In some embodiments, the low pH value is from 5.6 to 6.99. In some embodiments, the reference value is a reference labile proton exchange rate, wherein the reference labile proton exchange rate is from 100 to 200 exchanges/second. In some embodiments, the reference labile proton exchange rate is correlated to a reference pH value. In some embodiments, the reference pH value is from 7.0 to 7.2. In some embodiments, the condition is selected from intervertebral disc degeneration, discogenic pain, discogenic low back pain, chronic low back pain, low back pain, back pain, chronic back pain, progressive intervertebral disc degeneration, osteoarthritis, rheumatoid arthritis, an articular cartilage injury, temporomandibular disc degeneration and combinations thereof. In some embodiments, the imaged region of the subject's body comprises a joint or an intervertebral disc. In some embodiments, the condition is a painful condition. In some embodiments, the increased labile proton exchange rate is correlated with an upregulation of one or more pain-related factors in the subject. In some embodiments, the one or more pain-related factors are selected from bradykinin receptor B1 (BDKRB1), calcitonin gene-related peptide (CGRP), and catechol-0-methyltransferase (COMT). In some embodiments, the increased labile proton exchange rate is correlated with an upregulation of one or more inflammation-related factors in the subject. In some embodiments, the inflammation-related factor is interleukin-6 (IL-6). In some embodiments, the increased labile proton exchange rate is correlated with an upregulation of one or more neurogenic factors in the subject. In some embodiments, the neurogenic factor is brain-derived neurotrophic factor (BDNF) or nerve growth factor (NGF). In some embodiments, the quantitative chemical exchange saturation transfer (qCEST) sequence is a two dimension (2D) quantitative chemical exchange saturation transfer (qCEST) sequence. In some embodiments, the quantitative chemical exchange saturation transfer (qCEST) sequence is a three dimension (3D) quantitative chemical exchange saturation transfer (qCEST) sequence. In some embodiments, the MRI scanner is a 3.0 T MRI scanner. In some embodiments, the MRI scanner is a 1.5 T MRI scanner. In some embodiments, the MRI scanner is a 7.0 T MRI scanner. In some embodiments, the method further comprises determining that an origin of the subject's condition is within the imaged region of the subject's body where the physiological biomarker was measured. In some embodiments, the low pH value is indicative of the subject having the condition. In some embodiments, the method further comprises selecting one or more treatments for the subject if the condition is determined. In some embodiments, the method further comprises treating the subject with one or more treatments if the condition is determined.

BRIEF DESCRIPTION OF THE DRAWINGS

Exemplary embodiments are illustrated in referenced figures. It is intended that the embodiments and figures disclosed herein are to be considered illustrative rather than restrictive.

(FIG. 1B) phantoms with the same pH value (7.0) but varying GAG concentration (20 mM, 40 mM, 60 mM, 80 mM and 100 mM).

(FIG. 2A) Pixel-wise mapping of labile proton exchange rate. (FIG. 2B) Pixel-wise mapping of labile proton ratio. (FIG. 2C) The chemical exchange rate as a function of pH. (FIG. 2D) The labile proton ratio as a function of GAG concentration.

FIG. 3A-FIG. 3C depict in accordance with various embodiments of the invention, representative images of IVDs and corresponding exchange rate maps in one minipig. (FIG. 3A) T2-weighted image in the sagittal plane. (FIG. 3B) Axial anatomical images of corresponding IVDs. (FIG. 3C) Exchange rate maps of corresponding IVDs. The IVDs with lower pH tend to have higher exchange rates.

(FIG. 7A) The progress of IVD degeneration at 2, 6 and 10 weeks following puncture, as monitored by $T_2$-weighted sagittal MRI. White arrows denote the degenerated IVDs. Quantification of (FIG. 7B) $T_2$, (FIG. 7C) $T_1$, and (FIG. 7D) $T_{1\rho}$ mappings of degenerated IVDs compared to healthy controls at 2, 6 and 10 weeks following puncture (n=12 per experimental group; *p<0.05, ****p<0.0001). (FIG. 7E) Hematoxylin and eosin staining of representative IVDs that underwent degeneration at 2, 6 and 10 weeks after induction of degeneration, at low magnification (upper subfigures; scale bars, 1 mm) and high magnification (lower subfigures; scale bars, 100 μm).

FIG. 8A-FIG. 8D depict in accordance with various embodiments of the invention, pH and qCEST changes following IVD degeneration. (FIG. 8A) Correlation between the qCEST signal represented by the exchange rate between solute pool and water pool ($k_w$) and the pH measured within the IVD following animal sacrifice. (FIG. 8B) ROC curve analysis of qCEST signaling for the detection of degenerating IVDs. (FIG. 8C) pH and (FIG. 8D) qCEST measurements within the degenerating IVDs at 2, 6 and 10 weeks after degeneration. (n=12 per experimental group; *p<0.05, p<0.01, **p=0.0001; qCEST=quantitative chemical exchange saturation transfer).

FIG. 11A-FIG. 11E depict in accordance with various embodiments of the invention, Linear correlation between qCEST and biomarkers in degenerating IVDs. Correlation curves between qCEST signal and corresponding expression of (FIG. 11A) CGRP, (FIG. 11B) BDKRB1, (FIG. 11C) COMT, (FIG. 11D) IL-6 and (FIG. 11E) BDNF extracted from degenerated and healthy IVDs.

DETAILED DESCRIPTION OF THE INVENTION

Figure 1A:
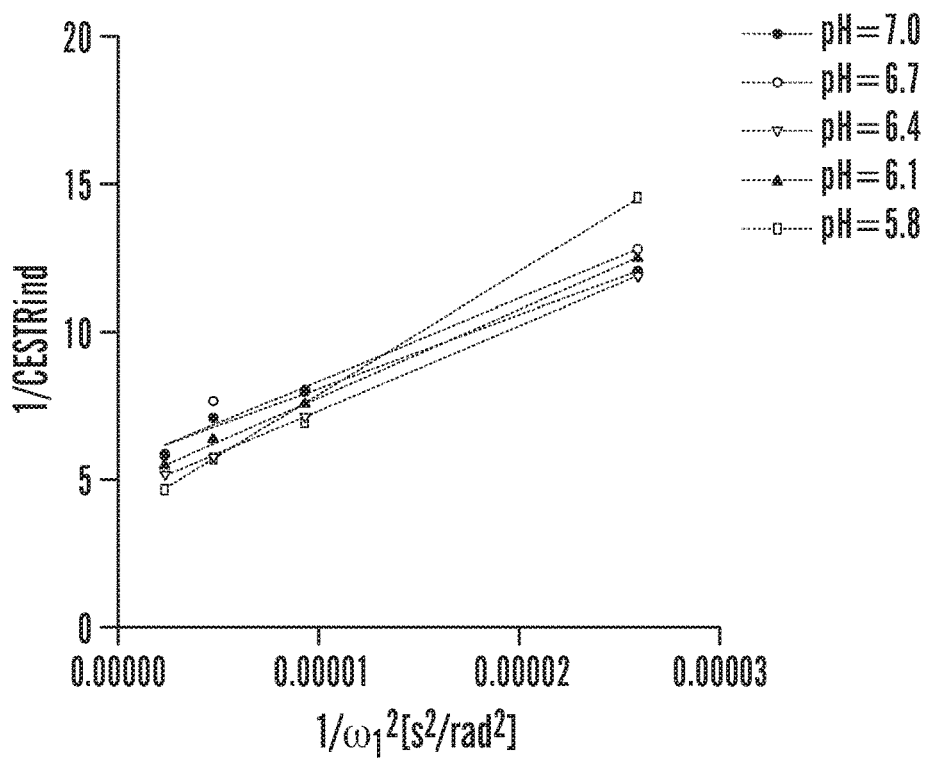
FIG. 1A-FIG. 1B depict in accordance with various embodiments of the invention, Ω-plots analysis of (FIG. 1A) phantoms with the same concentration (60 mM) but varying pH values (5.8, 6.1, 6.4, 6.7 and 7.0)

All references cited herein are incorporated by reference in their entirety as though fully set forth. Unless otherwise defined, all technical and scientific terms used herein have the same meaning as commonly understood by one of ordinary skill in the art to which this invention belongs. Westbrook et al., *MRI in Practice* $4^{th}$ *ed.*, and Guyton and Hall, *Textbook of Medical Physiology* $12^{th}$ *ed*, provide one skilled in the art with a general guide to many of the terms used in the present application.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims.

As used herein the term "comprising" or "comprises" is used in reference to compositions, methods, systems, articles of manufacture, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the terms "treat," "treatment," "treating," or "amelioration" when used in reference to a disease, disorder, condition, disease condition, or medical condition, refer to both therapeutic treatment and prophylactic or preventative measures, wherein the object is to reverse, alleviate, ameliorate, inhibit, lessen, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease, disorder, condition, disease condition, or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented. Non-limiting examples of treatments or therapeutic treatments include pharmacological, biological, cell and gene therapies and/or interventional surgical treatments. Non-limiting examples of a treatment or therapeutic treatment are pharmacological treatments. Non-limiting examples of a treatment or therapeutic treatment are biological treatments. Non-limiting examples of a treatment or therapeutic treatment are cell treatments. Non-limiting examples of a treatment or therapeutic treatment are gene therapies. Non-limiting examples of a treatment or therapeutic treatment are interventional surgical treatments. A treatment or therapeutic treatment may include one or more treatments or a combination of treatments.

"Beneficial results" or "desired results" may include, but are in no way limited to, lessening or alleviating the severity of the disease, disorder, condition, disease condition, or medical condition, preventing the disease, disorder, condition, disease condition, or medical condition from worsening, curing the disease, disorder, condition, disease condition, or medical condition, preventing the disease, disorder, condition, disease condition, or medical condition from developing, lowering the chances of a patient developing the disease, disorder, condition, disease condition, or medical condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of a disease, disorder, condition, disease condition, or medical condition, delay or slowing of a disease, disorder, condition, disease condition, or medical condition, and amelioration or palliation of symptoms associated with a disease, disorder, condition, disease condition, or medical condition.

As used herein, the term "administering," refers to the placement an agent or a treatment as disclosed herein into a subject by a method or route which results in at least partial localization of the agent or treatment at a desired site. "Route of administration" may refer to any administration pathway known in the art, including but not limited to aerosol, nasal, via inhalation, oral, anal, intra-anal, peri-anal, transmucosal, transdermal, parenteral, enteral, topical or local. "Parenteral" refers to a route of administration that is generally associated with injection, including intracranial, intraventricular, intrathecal, epidural, intradural, intraorbital, infusion, intracapsular, intracardiac, intradermal, intramuscular, intraperitoneal, intrapulmonary, intraspinal, intrasternal, intrathecal, intrauterine, intravascular, intravenous, intraarterial, subarachnoid, subcapsular, subcutaneous, transmucosal, or transtracheal.

"Diagnostic" means identifying the presence or nature of a pathologic condition and includes identifying patients who are at risk of developing a specific disease, disorder, condition, disease condition, or medical condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

By "at risk of" is intended to mean at increased risk of, compared to a normal subject, or compared to a control group, e.g. a patient population. Thus a subject carrying a particular marker may have an increased risk for a specific disease, disorder, condition, disease condition, or medical condition, and be identified as needing further testing. "Increased risk" or "elevated risk" mean any statistically significant increase in the probability, e.g., that the subject has the disease, disorder, condition, disease condition, or medical condition. The risk is preferably increased by at least 10%, more preferably at least 20%, and even more preferably at least 50% over the control group with which the comparison is being made.

The term "statistically significant" or "significantly" refers to statistical evidence that there is a difference. It is defined as the probability of making a decision to reject the null hypothesis when the null hypothesis is actually true. The decision is often made using the p-value.

The terms "detection", "detecting" and the like, may be used in the context of detecting a disease, disorder, condition, disease condition, or medical condition (e.g. when positive assay results are obtained). In the latter context, "detecting" and "diagnosing" are considered synonymous.

The term "diagnosis," or "dx," refers to the identification of the nature and cause of a certain phenomenon. As used herein, a diagnosis typically refers to a medical diagnosis, which is the process of determining which disease, disorder, condition, disease condition, or medical condition explains a symptoms and signs. A diagnostic procedure, often a diagnostic test or assay, can be used to provide a diagnosis. A diagnosis can comprise detecting the presence of a disease, disorder, condition, disease condition, or medical condition or the risk of getting a disease, disorder, condition, disease condition, or medical condition.

The term "prognosis," or "px," as used herein refers to predicting the likely outcome of a current standing. For example, a prognosis can include the expected duration and course of a disease, disorder, condition, disease condition, or medical condition, such as progressive decline or expected recovery.

The term "theranosis," or "tx" as used herein refers to a diagnosis or prognosis used in the context of a medical treatment. For example, theranostics can include diagnostic testing used for selecting appropriate and optimal therapies (or the inverse) based on the context of genetic content or other molecular or cellular analysis. Theranostics includes pharmacogenomics, personalized and precision medicine.

As used herein, a "subject" means a human or animal. For example, the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets. In an embodiment, the subject is a human.

"Mammal," as used herein, refers to any member of the class Mammalia, including, without limitation, humans and nonhuman primates such as chimpanzees and other apes and monkey species; farm animals such as cattle, sheep, pigs, goats and horses; domesticated mammals, such as dogs and cats; laboratory animals including rodents such as mice, rats and guinea pigs, and the like. The term does not denote a particular age or sex. Thus, adult and newborn subjects, whether male or female, are intended to be included within the scope of this term. Unless otherwise indicated, the subjects described herein can include mammals.

A subject can be one who has been previously diagnosed with or identified as suffering from or having a disease, disorder, condition, disease condition, or medical condition in need of treatment or one or more complications related to the disease, disorder, condition, disease condition, or medical condition, and optionally, have already undergone treatment for the disease, disorder, condition, disease condition, or medical condition or the one or more complications related to the disease, disorder, condition, disease condition, or medical condition. Alternatively, a subject can also be one who has not been previously diagnosed as having a disease, disorder, condition, disease condition, or medical condition or one or more complications related to the disease, disorder, condition, disease condition, or medical condition. For example, a subject can be one who exhibits one or more risk factors for a disease, disorder, condition, disease condition, or medical condition or one or more complications related to the disease, disorder, condition, disease condition, or medical condition or a subject who does not exhibit risk factors. For example, a subject can be one who exhibits one or more symptoms for a disease, disorder, condition, disease condition, or medical condition or one or more complications related to the disease, disorder, condition, disease condition, or medical condition or a subject who does not exhibit symptoms. A "subject in need" of diagnosis or treatment for a particular disease, disorder, condition, disease condition, or medical condition can be a subject suspected of having that disease, disorder, condition, disease condition, or medical condition, diagnosed as having that disease, disorder, condition, disease condition, or medical condition, already treated or being treated for that disease, disorder, condition, disease condition, or medical condition, not treated for that disease, disorder, condition, disease condition, or medical condition, or at risk of developing that disease, disorder, condition, disease condition, or medical condition.

"Sample" is used herein in its broadest sense. The term "biological sample" as used herein denotes a sample taken or isolated from a biological organism. A sample or biological sample may comprise a bodily fluid including blood, serum, plasma, tears, aqueous and vitreous humor, spinal fluid; a soluble fraction of a cell or tissue preparation, or media in which cells were grown; or membrane isolated or extracted from a cell or tissue; polypeptides, or peptides in solution or bound to a substrate; a cell; a tissue; a tissue print; a fingerprint, skin or hair; fragments and derivatives thereof. Non-limiting examples of samples or biological samples include cheek swab; mucus; whole blood, blood, serum; plasma; urine; saliva; semen; lymph; fecal extract; sputum; other body fluid or biofluid; cell sample; and tissue sample etc. The term also includes a mixture of the above-mentioned samples or biological samples. The term "sample" also includes untreated or pretreated (or pre-processed) biological samples. In some embodiments, a sample or biological sample can comprise one or more cells from the subject. In some embodiments, a sample or biological sample can comprise one or more tissue samples from the subject.

"Optional" or "optionally" means that the subsequently described circumstance may or may not occur, so that the description includes instances where the circumstance occurs and instances where it does not.

"Upregulation" means an increase in gene expression.

"Downregulation" means a decrease in gene expression.

Methods of the Invention

In various embodiments, the invention provides a method comprising imaging a region of a subject's body with a magnetic resonance imaging (MRI) scanner; and measuring one or more physiological biomarkers within the imaged region, wherein (a) the physiological biomarkers include a labile proton ratio ($f_r$) between a solute pool and a water pool and/or an exchange rate ($k_{sw}$) between the solute pool and the water pool. In some embodiments, the region is imaged using a quantitative chemical exchange saturation transfer (qCEST) sequence.

In various embodiments, the invention provides method for diagnosing a condition in a subject, the method comprising: imaging a region of a subject's body with a magnetic resonance imaging (MRI) scanner, wherein the region is imaged using a quantitative chemical exchange saturation transfer (qCEST) sequence; and measuring one or more physiological biomarkers within the imaged region, wherein the physiological biomarkers comprise a labile proton exchange rate ($k_{sw}$) between a solute pool and a water pool.

In various embodiments, the invention provides method for diagnosing a condition in a subject, the method comprising: imaging a region of a subject's body with a magnetic resonance imaging (MRI) scanner, wherein the region is imaged using a quantitative chemical exchange saturation transfer (qCEST) sequence; measuring one or more physiological biomarkers within the imaged region, wherein the physiological biomarkers comprise a labile proton exchange rate ($k_{sw}$) between a solute pool and a water pool; and determining that the subject has the condition if the labile proton exchange rate is increased relative to a reference value. In some embodiments, the method further comprises selecting one or more treatments for the subject if the condition is determined. In some embodiments, the treatments are selected from pharmacological, biological, cell and gene therapies and/or interventional surgical treatments. In some embodiments, the increased labile proton exchange rate is correlated to a low pH value. In some embodiments, the increased labile proton exchange rate is greater than 200 exchanges/second. In some embodiments, the increased labile proton exchange rate is from 201 to 1000 exchanges/second. In some embodiments, the low pH value is from 5.6 to 6.99. In some embodiments, the reference value is a reference labile proton exchange rate, wherein the reference labile proton exchange rate is from 100 to 200 exchanges/second. In some embodiments, the reference labile proton exchange rate is correlated to a reference pH value. In some embodiments, the reference pH value is from 7.0 to 7.2 In some embodiments, the condition is selected from intervertebral disc degeneration, discogenic pain, discogenic low back pain, chronic low back pain, low back pain, back pain, chronic back pain, progressive intervertebral disc degeneration, osteoarthritis, rheumatoid arthritis, an articular cartilage injury, temporomandibular disc degeneration and combinations thereof. In some embodiments, the imaged region of the subject's body comprises a joint or an intervertebral disc. In some embodiments, the condition is a painful condition. In some embodiments, the increased labile proton exchange rate is correlated with an upregulation of one or more pain-related factors in the subject. In some embodiments, the one or more pain-related factors are selected from bradykinin receptor B1 (BDKRB1), calcitonin gene-related peptide (CGRP), and catechol-0-methyltransferase (COMT). In some embodiments, the increased labile proton exchange rate is correlated with an upregulation of one or more inflammation-related factors in the subject. In some embodiments, the inflammation-related factor is interleukin-6 (IL-6). In some embodiments, the increased labile proton exchange rate is correlated with an upregulation of one or more neurogenic factors in the subject. In some embodiments, the neurogenic factor is brain-derived neurotrophic factor (BDNF) or nerve growth factor (NGF). In some embodiments, the quantitative chemical exchange saturation transfer (qCEST) sequence is a two dimension (2D) quantitative chemical exchange saturation transfer (qCEST) sequence. In some embodiments, the quantitative chemical exchange saturation transfer (qCEST) sequence is a three dimension (3D) quantitative chemical exchange saturation transfer (qCEST) sequence. In some embodiments, the MRI scanner is a 3.0 T MRI scanner. In some embodiments, the MRI scanner is a 1.5 T MRI scanner. In some embodiments, the MRI scanner is a 7.0 T MRI scanner. In some embodiments, further comprising determining that an origin of the subject's condition is within the imaged region of the subject's body where the physiological biomarker was measured. In some embodiments, the low pH value is indicative of the subject having the condition. In some embodiments, the method further comprises selecting one or more treatments for the subject if the condition is determined. In some embodiments, the method further comprises treating the subject with one or more treatments if the condition is determined.

In various embodiments, the invention provides a method for treating a subject diagnosed with a condition, wherein the subject was diagnosed with the condition by a method comprising: imaging a region of a subject's body with a magnetic resonance imaging (MRI) scanner, wherein the region is imaged using a quantitative chemical exchange saturation transfer (qCEST) sequence; measuring one or more physiological biomarkers within the imaged region, wherein the physiological biomarkers comprise a labile proton exchange rate ($k_{sw}$) between a solute pool and a water pool; determining that the subject has the condition if the labile proton exchange rate is increased relative to a reference value; selecting a treatment for the subject; and treating the subject with the treatment.

In various embodiments, the invention provides a method for treating a subject diagnosed with a condition, wherein the subject was diagnosed with the condition by a method comprising: imaging a region of a subject's body with a magnetic resonance imaging (MRI) scanner, wherein the region is imaged using a quantitative chemical exchange saturation transfer (qCEST) sequence; measuring one or more physiological biomarkers within the imaged region, wherein the physiological biomarkers comprise a labile proton ratio ($f_r$) between a solute pool and a water pool and/or an exchange rate ($k_{sw}$) between the solute pool and the water pool; selecting a treatment for the subject; and treating the subject with the treatment.

In various embodiments, the invention provides a method for treating a subject diagnosed with a condition, comprising requesting the diagnosis results so that the subject may be treated; selecting a treatment for the subject; and treating the subject based on the diagnosis results, wherein the subject was diagnosed with the condition by a method comprising: imaging a region of a subject's body with a magnetic resonance imaging (MI) scanner, wherein the region is imaged using a quantitative chemical exchange saturation transfer (qCEST) sequence; measuring one or more physiological biomarkers within the imaged region, wherein the physiological biomarkers comprise a labile proton exchange rate ($k_{sw}$) between a solute pool and a water pool; and determining that the subject has the condition if the labile proton exchange rate is increased relative to a reference value.

In various embodiments, the invention provides a method for treating a subject diagnosed with a condition, comprising requesting the diagnosis results so that the subject may be treated; selecting a treatment for the subject; and treating the subject based on the diagnosis results, wherein the subject was diagnosed with the condition by a method comprising: imaging a region of a subject's body with a magnetic resonance imaging (MRI) scanner, wherein the region is imaged using a quantitative chemical exchange saturation transfer (qCEST) sequence; and measuring one or more physiological biomarkers within the imaged region, wherein the physiological biomarkers comprise a labile proton ratio ($f_r$) between a solute pool and a water pool and/or an exchange rate ($k_{sw}$) between the solute pool and the water pool.

A method for prognosing a condition in a subject, the method comprising: imaging a region of a subject's body with a magnetic resonance imaging (MRI) scanner, wherein the region is imaged using a quantitative chemical exchange saturation transfer (qCEST) sequence; measuring one or more physiological biomarkers within the imaged region, wherein the physiological biomarkers comprise a labile proton exchange rate ($k_{sw}$) between a solute pool and a water pool; and comparing a measurement of one or more physiological biomarkers to a previous measurement of the same one or more physiological biomarkers, wherein an increase in the labile proton exchange rate over time is a poor prognosis of the condition. In some embodiments, the method further comprises selecting one or more treatments for the subject based on the prognosis of the condition. In some embodiments, the method further comprises treating the subject with one or more treatments based on the prognosis of the condition. In some embodiments, a low pH value is indicative of a poor prognosis of the condition.

A method for prognosing a condition associated with tissue degeneration and/or pain in a subject, comprising: imaging a region of a subject's body, wherein the region is imaged using a quantitative chemical exchange saturation transfer (qCEST) sequence; measuring one or more physiological biomarkers within the imaged region, wherein the physiological biomarkers comprise a labile proton exchange rate ($k_{sw}$) between a solute pool and a water pool; and prognosing the condition by comparing measurements of one or more physiological biomarkers measured within the imaged region to previous measurements of the same one or more physiological biomarkers measured within the imaged region.

A method for prognosing a condition associated with tissue degeneration and/or pain in a subject, comprising: imaging a region of a subject's body, wherein the region is imaged using a quantitative chemical exchange saturation transfer (qCEST) sequence; measuring one or more physiological biomarkers within the imaged region, wherein the physiological biomarkers comprise a labile proton ratio ($f_r$) between a solute pool and a water pool and/or an exchange rate ($k_{sw}$) between the solute pool and the water pool; and prognosing the condition by comparing measurements of one or more physiological biomarkers measured within the imaged region to previous measurements of the same one or more physiological biomarkers measured within the imaged region.

In various embodiments, the invention provides method for detecting a condition in a subject, the method comprising: imaging a region of a subject's body with a magnetic resonance imaging (MRI) scanner, wherein the region is imaged using a quantitative chemical exchange saturation transfer (qCEST) sequence; measuring one or more physiological biomarkers within the imaged region, wherein the physiological biomarkers comprise a labile proton exchange rate ($k_{sw}$) between a solute pool and a water pool; and determining that the subject has the condition if the labile proton exchange rate is increased relative to a reference value. In some embodiments, the method further comprises selecting one or more treatments for the subject if the condition is determined. In some embodiments, the treatments are selected from pharmacological, biological, cell and gene therapies and/or interventional surgical treatments. In some embodiments, the method further comprises treating the subject with one or more treatments if the condition is determined.

In various embodiments, the invention provides method for detecting a condition in a subject, the method comprising: imaging a region of a subject's body with a magnetic resonance imaging (MRI) scanner, wherein the region is imaged using a quantitative chemical exchange saturation transfer (qCEST) sequence; measuring one or more physiological biomarkers within the imaged region, wherein the physiological biomarkers comprise a labile proton ratio ($f_r$) between a solute pool and a water pool and/or an exchange rate ($k_{sw}$) between the solute pool and the water pool. In some embodiments, the method further comprises selecting one or more treatments for the subject if the condition is determined. In some embodiments, the treatments are selected from pharmacological, biological, cell and gene therapies and/or interventional surgical treatments. In some embodiments, the method further comprises treating the subject with one or more treatments if the condition is determined.

In some embodiments, the one or more magnetic resonance images are obtained over a period of time. In some embodiments, the one or more magnetic resonance images are obtained at different times. In some embodiments, the one or more magnetic resonance images are obtained contemporaneously. In some embodiments, the one or more magnetic resonance images are two or more magnetic resonance images. In some embodiments, the period of time is measured in milliseconds, seconds, minutes, hours, days, months, or years, or combinations thereof.

In some embodiments, the invention provides a method for determining the risk of developing a condition in a subject, comprising imaging a region of a subject's body with a magnetic resonance imaging (MRI) scanner, wherein the region is imaged using a quantitative chemical exchange saturation transfer (qCEST) sequence; measuring one or more physiological biomarkers within the imaged region, wherein the physiological biomarkers include a labile proton exchange rate ($k_{sw}$) between a solute pool and a water pool; and comparing the labile proton exchange rate from the subject to a reference value, wherein an increase in the labile exchange rate from the subject compared to the reference value is indicative of an increased risk of the subject developing the condition. In some embodiments, the low pH value is indicative of the increased risk of the subject developing the condition. In some embodiments, the method further comprises selecting one or more treatments for the subject based on the increased risk of the subject developing the condition. In some embodiments, the method further comprises treating the subject with one or more treatments based on the increased risk of the subject developing the condition.

In some embodiments, the method further comprises comparing the labile proton exchange rate from the subject to a reference value, wherein an increase in the labile exchange rate from the subject compared to the reference value is an assessment of the subject, wherein the assessment is a prognosis of developing a condition. In some embodiments, the method further comprises comparing the labile proton exchange rate from the subject to a reference value, wherein an increase in the labile exchange rate from the subject compared to the reference value is an assessment of the subject, wherein the assessment is a diagnosis of a condition. In some embodiments, the method further comprises comparing the labile proton exchange rate from the subject to a reference value, wherein an increase in the labile exchange rate from the subject compared to the reference value is an assessment of the subject is indicative of a condition. In some embodiments, the method further comprises treating the subject based on the assessment. In some embodiments, the method further comprises selecting one or more treatments for the subject based on the assessment. In some embodiments, the method further comprises treating the subject with one or more treatments based on the assessment.

In some embodiments, the invention provides a method for determining the risk of developing a condition in a subject, comprising imaging a region of a subject's body with a magnetic resonance imaging (MRI) scanner, wherein the region is imaged using a quantitative chemical exchange saturation transfer (qCEST) sequence; measuring one or more physiological biomarkers within the imaged region, wherein the physiological biomarkers include a labile proton exchange rate ($k_{sw}$) between a solute pool and a water pool; and comparing the labile proton exchange rate from the subject to a reference value, wherein an increase in the labile exchange rate from the subject compared to the reference value is indicative of an increased risk of the subject developing the condition. In some embodiments, the low pH value is indicative of the increased risk of the subject developing the condition. In some embodiments, the method further comprises selecting one or more treatments for the subject based on the increased risk of the subject developing the condition. In some embodiments, the method further comprises treating the subject with one or more treatments based on the increased risk of the subject developing the condition In some embodiments, the increased labile proton exchange rate is correlated with an upregulation of one or more pain-related factors in the subject. In some embodiments, the pain-related factors (pain-related markers) are selected from bradykinin receptor B (BDKRB1), calcitonin gene-related peptide (CGRP) and catechol-0-methyltransferase (COMT). In some embodiments, the pain-related factor is bradykinin receptor B1 (BDKRB1). In some embodiments, the pain-related factor is calcitonin gene-related peptide (CGRP). In some embodiments, the pain-related factor is catechol-0-methyltransferase (COMT). In some embodiments, the method further comprises determining that an origin of the subject's pain associated with the condition is within the region of the subject's body where the expression of one or more pain-related factors (pain-related markers) is detected. In some embodiments, the condition is a painful condition.

In some embodiments, the increased labile proton exchange rate is correlated with an upregulation of one or more inflammation-related factors in the subject. In some embodiments, the inflammatory factors (inflammation-related markers or inflammation-related factors) are selected from interleukin-6 (IL-6). In some embodiments, the method further comprises determining that an origin of the subject's pain associated with the condition is within the region of the subject's body where the expression of one or more inflammatory factors (inflammation-related markers) is detected. In some embodiments, the condition is a painful condition.

In some embodiments, the increased labile proton exchange rate is correlated with an upregulation of one or more neurogenic factors in the subject. In some embodiments, the neurogenic factors (neurogenic markers) are selected from brain-derived neurotrophic factor (BDNF) and nerve growth factor (NGF). In some embodiments, the method further comprises determining that an origin of the subject's pain associated with the condition is within the region of the subject's body where the expression of one or more neurogenic factors (neurogenic markers) is detected. In some embodiments, the condition is a painful condition In some embodiments, the physiological biomarkers comprise a labile proton ratio ($f_r$) between a solute pool and a water pool and/or an exchange rate ($k_{sw}$) between the solute pool and the water pool. In some embodiments, the physiological biomarkers comprise a labile proton ratio ($f_r$) between a solute pool and a water pool and/or a labile proton exchange rate ($k_{sw}$) between the solute pool and the water pool. In some embodiments, the physiological biomarkers comprise a labile proton ratio ($f_r$) between a solute pool and a water pool and a labile proton exchange rate ($k_{sw}$) between the solute pool and the water pool. In some embodiments, the physiological biomarkers comprise a labile proton ratio ($f_r$) between a solute pool and a water pool or a labile proton exchange rate ($k_{sw}$) between the solute pool and the water pool. In some embodiments, the physiological biomarkers comprise a labile proton ratio ($f_r$) between a solute pool and a water pool. In some embodiments, the physiological biomarkers comprise an exchange rate ($k_{sw}$) between a solute pool and a water pool. In some embodiments, the physiological biomarkers comprise a labile proton exchange rate ($k_{sw}$) between a solute pool and a water pool.

In certain embodiments, the abnormal physiological states may include, but are in no way limited to, low pH and/or low GAG concentration compared to a normal subject without the condition. In certain embodiments, the abnormal physiological state is low GAG concentration compared to a normal subject without the condition. In certain embodiments, the abnormal physiological state is low GAG concentration. In some embodiments, the abnormal physiological state is low pH compared to a normal subject without the condition. In some embodiments, the GAG concentration is relative to a healthy, non-degenerate disc. In some embodiments, the low pH concentration is relative to a healthy, non-degenerate disc. In some embodiments, the GAG concentration is relative to a healthy, non-degenerate disc in the subject. In some embodiments, the low pH concentration is relative to a healthy, non-degenerate disc in the subject. In some embodiments, the normal subject is the subject, wherein the subject does not have a condition. In some embodiments, the normal subject is the subject before the subject is treated for a condition. In some embodiments, the normal subject is the subject that has been treated for a condition. In some embodiments, the normal subject is the subject at an earlier time point (earlier point in time).

In certain embodiments, the abnormal physiological state is low pH compared to a normal subject without the condition. In certain embodiments, the abnormal physiological state is low pH. In some embodiments, the abnormal physiological state is low pH compared to a pH value obtained from a pH reference sample (reference pH value). In some embodiments, low pH (low pH value) is 5.6-6.99. In some embodiments, low pH (low pH value) is 5.6-5.7, 5.6-5.8, 5.6-5.9, 5.6-6.0, 5.6-6.1, 5.6-6.2, 5.6-6.3, 5.6-6.4, 5.6-6.5, 5.6-6.6, 5.6-6.7, 5.6-6.8, 5.6-6.9, or 5.6-6.99.

In some embodiments, low pH (low pH value) is 5.60 to 6.99, 5.60 to 6.90, 5.60 to 6.80, 5.60 to 6.70, 5.60 to 6.60, 5.60 to 6.50, 5.60 to 6.40, 5.60 to 6.30, 5.60 to 6.20, 5.60 to 6.10, 5.60 to 6.00, 5.60 to 5.90, 5.60 to 5.80, 5.60 to 5.70, 5.70 to 6.99, 5.70 to 6.90, 5.70 to 6.80, 5.70 to 6.70, 5.70 to 6.60, 5.70 to 6.50, 5.70 to 6.40, 5.70 to 6.30, 5.70 to 6.20, 5.70 to 6.10, 5.70 to 6.00, 5.70 to 5.90, 5.70 to 5.80, 5.80 to 6.99, 5.80 to 6.90, 5.80 to 6.80, 5.80 to 6.70, 5.80 to 6.60, 5.80 to 6.50, 5.80 to 6.40, 5.80 to 6.30, 5.80 to 6.20, 5.80 to 6.10, 5.80 to 6.00, 5.80 to 5.90, 5.90 to 6.99, 5.90 to 6.90, 5.90 to 6.80, 5.90 to 6.70, 5.90 to 6.60, 5.90 to 6.50, 5.90 to 6.40, 5.90 to 6.30, 5.90 to 6.20, 5.90 to 6.10, 5.90 to 6.00, 6.00 to 6.99, 6.00 to 6.90, 6.00 to 6.80, 6.00 to 6.70, 6.00 to 6.60, 6.00 to 6.50, 6.00 to 6.40, 6.00 to 6.30, 6.00 to 6.20, 6.00 to 6.10, 6.10 to 6.99, 6.10 to 6.90, 6.10 to 6.80, 6.10 to 6.70, 6.10 to 6.60, 6.10 to 6.50, 6.10 to 6.40, 6.10 to 6.30, 6.0 to 6.20, 6.20 to 6.99, 6.20 to 6.90, 6.20 to 6.80, 6.20 to 6.70, 6.20 to 6.60, 6.20 to 6.50, 6.20 to 6.40, 6.20 to 6.30, 6.30 to 6.99, 6.30 to 6.90, 6.30 to 6.80, 6.30 to 6.70, 6.30 to 6.60, 6.30 to 6.50, 6.30 to 6.40, 6.40 to 6.99, 6.40 to 6.90, 6.40 to 6.80, 6.40 to 6.70, 6.40 to 6.60, 6.40 to 6.50, 6.50 to 6.99, 6.50 to 6.90, 6.50 to 6.80, 6.50 to 6.70, 6.50 to 6.60, 6.60 to 6.99, 6.60 to 6.90, 6.60 to 6.80, 6.60 to 6.70, 6.70 to 6.99, 6.70 to 6.90, 6.70 to 6.80, 6.80 to 6.99, 6.80 to 6.90, or 6.90 to 6.99.

In certain embodiments, the reference pH value is from 7.0 to 7.2. In some embodiments, the reference pH value is from 7.00 to 7.20, 7.00 to 7.15, 7.00 to 7.10, 7.00 to 7.05, 7.05 to 7.20, 7.05 to 7.15, 7.05 to 7.10, 7.10 to 7.20, 7.10 to 7.15, or 7.15 to 7.20.

In some embodiments, the increased labile proton exchange rate is greater than 200 exchanges/second. In some embodiments, the increased labile proton exchange rate is from 201 to 1000 exchanges/second. In some embodiments, the increased labile proton exchange rate is from 201 to 1000, 201 to 950, 201 to 900, 201 to 850, 201 to 800, 201 to 750, 201 to 700, 201 to 650, 201 to 600, 201 to 550, 201 to 500, 201 to 450, 201 to 400, 201 to 350, 201 to 300, 201 to 250, 250 to 1000, 250 to 950, 250 to 900, 250 to 850, 250 to 800, 250 to 750, 250 to 700, 250 to 650, 250 to 600, 250 to 550, 250 to 500, 250 to 450, 250 to 400, 250 to 350, 250 to 300, 300 to 1000, 300 to 950, 300 to 900, 300 to 850, 300 to 800, 300 to 750, 300 to 700, 300 to 650, 300 to 600, 300 to 550, 300 to 500, 300 to 450, 300 to 400, 300 to 350, 350 to 1000, 350 to 950, 350 to 900, 350 to 850, 350 to 800, 350 to 750, 350 to 700, 350 to 650, 350 to 600, 350 to 550, 350 to 500, 350 to 450, 350 to 400, 400 to 1000, 400 to 950, 400 to 900, 400 to 850, 400 to 800, 400 to 750, 400 to 700, 400 to 650, 400 to 600, 400 to 550, 400 to 500, 400 to 450, 450 to 1000, 450 to 950, 450 to 900, 450 to 850, 450 to 800, 450 to 750, 450 to 700, 450 to 650, 450 to 600, 450 to 550, 450 to 500, 500 to 1000, 500 to 950, 500 to 900, 500 to 850, 500 to 800, 500 to 750, 500 to 700, 500 to 650, 500 to 600, 500 to 550, 550 to 1000, 550 to 950, 550 to 900, 550 to 850, 550 to 800, 550 to 750, 550 to 700, 550 to 650, 550 to 600, 600 to 1000, 600 to 950, 600 to 900, 600 to 850, 600 to 800, 600 to 750, 600 to 700, 600 to 650, 650 to 1000, 650 to 950, 650 to 900, 650 to 850, 650 to 800, 650 to 750, 650 to 700, 700 to 1000, 700 to 950, 700 to 900, 700 to 850, 700 to 800, 700 to 750, 750 to 1000, 750 to 950, 750 to 900, 750 to 850, 750 to 800, 800 to 1000, 800 to 950, 800 to 900, 800 to 850, 850 to 1000, 850 to 950, 850 to 900, 900 to 1000, 900 to 950, or 950 to 1000 exchanges/second.

In some embodiments, the reference value is a reference labile proton exchange rate, wherein the reference labile proton exchange rate is from 100 to 200 exchanges/second. In some embodiments, the reference labile proton exchange rate is from 100 to 200, 100 to 190, 100 to 180, 100 to 170, 100 to 160, 100 to 150, 100 to 140, 100 to 130, 100 to 120, 100 to 110, 110 to 200, 110 to 190, 110 to 180, 110 to 170, 110 to 160, 110 to 150, 110 to 140, 110 to 130, 110 to 120, 120 to 200, 120 to 190, 120 to 180, 120 to 170, 120 to 160, 120 to 150, 120 to 140, 120 to 130, 130 to 200, 130 to 190, 130 to 180, 130 to 170, 130 to 160, 130 to 150, 130 to 140, 140 to 200, 140 to 190, 140 to 180, 140 to 170, 140 to 160, 140 to 150, 150 to 200, 150 to 190, 150 to 180, 150 to 170, 150 to 160, 160 to 200, 160 to 190, 160 to 180, 160 to 170, 170 to 200, 170 to 190, 170 to 180, 180 to 200, 180 to 190, or 190 to 200 exchanges/second.

In some embodiments, the reference value is obtained from a normal subject that does not have a condition. In some embodiments, the reference value is obtained from a control subject, wherein the control subject does not have a condition. In some embodiments, the reference value is obtained from the subject, wherein the subject does not have a condition. In some embodiments, the reference value is obtained from the subject before the subject is treated for a condition. In some embodiments, the reference value is obtained from a subject that has been treated for a condition. In some embodiments, the reference value is obtained from the subject at an earlier time point (earlier point in time).

In some embodiments, the imaged region of the subject's body includes the subject's spine or vertebral column or backbone or a section or component thereof. In some embodiments, the imaged region of the subject's body includes a joint or an intervertebral disc. In some embodiments, the imaged region of the subject's body is one or more joints. In some embodiments, the imaged region of the subject's body is one or more intervertebral discs.

In some embodiments, the condition may include, but is in no way limited to, intervertebral disc degeneration, discogenic pain, osteoarthritis, rheumatoid arthritis, an articular cartilage injury, temporomandibular disc degeneration and combinations thereof. In some embodiments the condition is selected from intervertebral disc degeneration, discogenic pain, discogenic low back pain, chronic low back pain, low back pain, back pain, chronic back pain, progressive intervertebral disc degeneration, osteoarthritis, rheumatoid arthritis, an articular cartilage injury, temporomandibular disc degeneration and combinations thereof. In certain embodiments, the condition is discogenic pain. In certain embodiments, the condition is discogenic low back pain. In certain embodiments, the condition is intervertebral disc degeneration. In some embodiments, the condition is a disease condition. In some embodiments, the condition is a medical condition. In some embodiments, the condition is a disorder. In some embodiments, the condition is a disease. In some embodiments, the condition is intervertebral disc degeneration. In some embodiments, the condition is osteoarthritis. In some embodiments, the condition is rheumatoid arthritis. In some embodiments, the condition is an articular cartilage injury. In some embodiments, the condition is temporomandibular disc degeneration. In some embodiments, the condition is chronic low back pain. In some embodiments, the condition is low back pain. In some embodiments, the condition is back pain. In some embodiments, the condition is chronic back pain. In some embodiments, the condition is progressive intervertebral disc degeneration. In some embodiments, the condition is a painful condition.

In certain embodiments, the method further includes determining that an origin of the subject's pain associated with the condition is within the region of the subject's body where one or more abnormal physiological states is detected.

In some embodiments, the magnetic resonance imaging technique is a chemical exchange saturation transfer (CEST) sequence. In some embodiments, the magnetic resonance imaging technique is a quantitative chemical exchange saturation transfer sequence (qCEST). In some embodiments, the region is imaged using a chemical exchange saturation transfer (CEST) sequence. In some embodiments the region is imaged using a quantitative chemical exchange saturation transfer sequence (qCEST). In some embodiments, the region is imaged using a two dimension (2D) reduced field-of-view (rFOV) turbo spin echo (TSE) chemical exchange saturation transfer (CEST) sequence. In some embodiments, the region is imaged using a two dimension (2D) reduced field-of-view (rFOV) turbo spin echo (TSE) quantitative chemical exchange saturation transfer (qCEST) sequence. In some embodiments, alternative CEST sequences may be used to measure the aforementioned physiological biomarkers. In some embodiments, alternative qCEST sequences may be used to measure the aforementioned physiological biomarkers. In some embodiments, the quantitative chemical exchange saturation transfer (qCEST) sequence is a two dimension (2D) quantitative chemical exchange saturation transfer (qCEST) sequence. In some embodiments, the quantitative chemical exchange saturation transfer (qCEST) sequence is a three dimension (3D) quantitative chemical exchange saturation transfer (qCEST) sequence.

In various embodiments, the imaging of a region of the subject's body with a magnetic resonance imaging (MRI) scanner is performed in vivo. In various embodiments, the magnetic resonance images from the subject are obtained in vivo.

The readout of the CEST sequences may include, but are in no way limited to, gradient echo (GRE), echo planar imaging (EPI), gradient and spin echo (GRASE) and balanced steady-state free precession (SSFP). The readout of the qCEST sequences may include, but are in no way limited to, gradient echo (GRE), echo planar imaging (EPI), gradient and spin echo (GRASE) and balanced steady-state free precession (SSFP). In certain embodiments, the method further includes diagnosing the subject with a condition characterized by pain and/or tissue degeneration, if the physiological biomarkers detected from imaging indicate one or more abnormal physiological states within the imaged region.

In some embodiments, the MRI scanner is a 7.0 T scanner. In certain embodiments, the MRI scanner is a 3.0 T MRI scanner. In some embodiments, the MRI scanner is a 1.5 T MRI scanner.

In certain embodiments, the imaging is performed by using reduced field-of-view (rFOV) excitation. In other embodiments, rFOV excitation is not used. In some embodiments, a slice thickness for the MRI scan is selected to be small enough to avoid fat signal interference. In certain embodiments, CEST MRI imaging parameters include: TR/TE=10500/10 ms, 2 averages, single shot. In certain embodiments, qCEST MRI imaging parameters include: TR/TE=10500/10 ms, 2 averages, single shot. In certain embodiments, CEST MRI imaging parameters include: TR/TE 1/4 10,500/10 ms, 2 averages, single shot. In certain embodiments, qCEST MRI imaging parameters include: TR/TE 1/4 10,500/10 ms, 2 averages, single shot. In some embodiments TR/TE=7000-16000/7-15 ms. In certain embodiments, for each IVD, images are acquired in the axial plane with a slice thickness of 3 mm, field of view (FOV) of 100×40 mm$^2$ and spatial resolution of 0.8×0.8 mm$^2$. In some embodiments, slice thickness is 2-4 mm, FOV is 80-160× 40-160 mm$^2$, and spatial resolution is 0.6-1 mm$^2$. In certain embodiments, for each IVD, images are acquired in the axial plane with a slice thickness of 3 mm, field of view of 140×40 mm$^2$ and spatial resolution of 1.1×1.1 mm$^2$. In certain embodiments, the CEST saturation module utilized in the imaging consists of 39 Gaussian-shaped pulses, with a duration $t_p$=80 ms for each pulse and an interpulse delay $t_d$=80 ms (duty cycle=50%, total saturation duration $T_s$=6240 ms) at saturation flip angle 900°, 1500°, 2100° and 3000° ($B_1$ amplitudes=flip angle/($\gamma t_p$))=0.73 μT, 1.22 μT, 1.71 μT and 2.45 μT; Gaussian saturation pulse parameters c1=0.50, c2=0.59). In certain embodiments, the qCEST saturation module utilized in the imaging consists of 39 Gaussian-shaped pulses, with a duration $t_p$=80 ms for each pulse and an interpulse delay $t_d$=80 ms (duty cycle=50%, total saturation duration $T_s$=6240 ms) at saturation flip angle 900°, 1500°, 2100° and 3000° ($B_1$ amplitudes=flip angle/($\gamma t_p$)=0.73 μT, 1.22 μT, 1.71 μT and 2.45 μT; Gaussian saturation pulse parameters c1=0.50, c2=0.59). In some embodiments, the CEST saturation module may have total saturation Ts=4000-8000 ms at saturation flip angle ranging from 600 to 3000°. In some embodiments, the qCEST saturation module may have total saturation Ts=4000-8000 ms at saturation flip angle ranging from 600 to 3000°. In certain embodiments, the Z-spectrum are acquired with different saturation frequencies, including but not limited to ±1.6, ±1.3, ±1.0, ±0.7, and ±0.4 ppm. In some embodiments, the scan time of the CEST experiment for each IVD was about 40 minutes. In some embodiments, the scan time of the qCEST experiment for each IVD was about 40 minutes.

As used herein, a physiological biomarker refers to, for example a pH value, a labile proton exchange rate ($k_{sw}$) between a solute pool and a water pool, or a labile proton ratio ($f_r$) between a solute pool and a water pool. The terms physiological biomarker and metabolic biomarker have the same meaning and are used interchangeably herein.

Systems and Computers

In various embodiments, the invention teaches a non-transitory computer-readable medium having computer-readable instructions for causing one or more processors of a magnetic resonance imaging (MRI) machine to execute a method that includes applying an MRI pulse sequence to a volume of interest (VOI) in a subject, wherein the VOI includes a joint or an intervertebral disc (IVD), or a portion thereof; acquiring magnetic resonance data from the volume of interest (VOI) in the subject; and measuring, based on the magnetic resonance data acquired, one or more physiological biomarkers within the imaged region, wherein (a) the physiological biomarkers include a labile proton ratio ($f_r$) between a solute pool and a water pool and/or an exchange rate ($k_{sw}$) between the solute pool and the water pool, for example as described herein in greater detail in the "Examples" section. In certain embodiments, the pulse sequence is a two dimension (2D) reduced field of view (rFOV) turbo spin echo (TSE) chemical exchange saturation transfer (CEST) sequence. In certain embodiments, the pulse sequence is a two dimension (2D) reduced field of view (rFOV) turbo spin echo (TSE) quantitative chemical exchange saturation transfer (qCEST) sequence. In some embodiments, the MRI scanner is a 7.0 T scanner. In certain embodiments, the MRI scanner is a 3.0 T MRI scanner. In some embodiments, the MRI scanner is a 1.5 T MRI scanner.

In various embodiments, the invention teaches a magnetic resonance imaging system that includes a magnet operable to provide a magnetic field; a transmitter operable to transmit to a region within the magnetic field; a receiver operable to receive a magnetic resonance signal from the region; one or more processor operable to control the transmitter and the receiver; and a non-transitory computer-readable medium having computer-readable instructions for causing one or more processor of the magnetic resonance imaging (MRI) system to execute a method that includes: applying a pulse sequence described herein to a volume of interest (VOI) in a subject, wherein the VOI includes a joint or an intervertebral disc (IVD) or a portion thereof; acquiring magnetic resonance data from the volume of interest (VOI) in the subject; and measuring, based on the magnetic resonance data acquired, one or more physiological biomarkers within the imaged region, wherein (a) the physiological biomarkers include a labile proton ratio ($f_r$) between a solute pool and a water pool and/or an exchange rate ($k_{sw}$) between the solute pool and the water pool.

Figure 5:
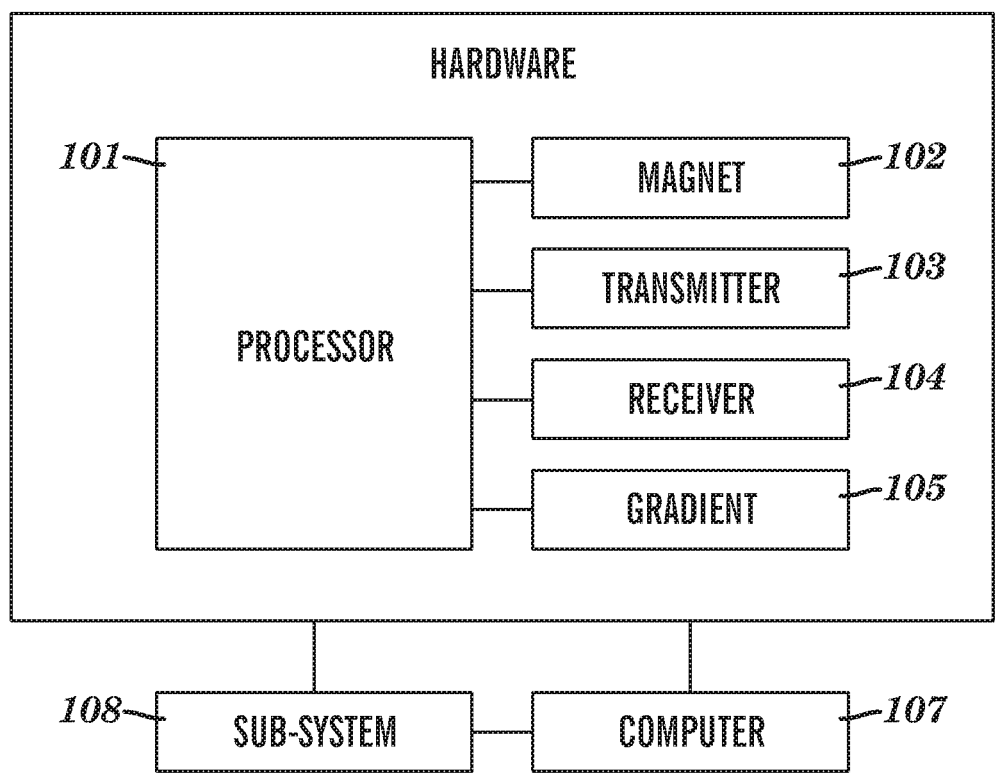
FIG. 5 depicts in accordance with various embodiments of the invention, a system including an MRI machine and a computing device, which are capable of executing the inventive methods.

One of skill in the art would readily appreciate that a number of different types of imaging systems could be used to perform the inventive methods described herein. Merely by way of example, the imaging systems described in the examples could be used. FIG. 5 also depicts a view of a system 100 that can be used to accomplish the inventive methods. System 100 includes hardware and computer 107. Hardware includes magnet 102, transmitter 103, receiver 104, and gradient 105, all of which are in communication with processor 101. Magnet 102 can include a permanent magnet, a superconducting magnet, or other type of magnet. Transmitter 103 along with receiver 104, are part of the RF system. Transmitter 103 can represent a radio frequency transmitter, a power amplifier, and an antenna (or coil). Receiver 104, as denoted in FIG. 5, can represent a receiver antenna (or coil) and an amplifier. In the example shown, transmitter 103 and receiver 104 are separately represented, however, in one example, transmitter 103 and receiver 104 can share a common coil. The hardware includes gradient 105. Gradient 105 can represent one or more coils used to apply a gradient for localization.

Processor 101, in communication with various elements of the hardware, includes one or more processors configured to implement a set of instructions corresponding to any of the methods disclosed herein. Processor 101 can be configured to implement a set of instructions (stored in memory of the hardware or sub-system 108) to provide RF excitation and gradients and receive magnetic resonance data from a volume of interest. Sub-system 108 can include hardware and software capable of facilitating the processing of data generated by the hardware, in conjunction with, or as a substitute for, the processing associated with image reconstruction that is normally handled by processor 101 in an MRI machine. One of skill in the art would readily appreciate that certain components of the imaging systems described herein, including the processor 101 and/or sub-system 108, are used to execute instructions embedded on a computer-readable medium to implement the inventive data acquisition, image reconstruction, and physiological biomarker evaluation methods described herein.

In some embodiments, computer 107 is operably coupled to the hardware and sub-system 108. Computer 107 can include one or more of a desktop computer, a workstation, a server, or a laptop computer. In one example, computer 107 is user-operable and includes a display, a printer, a network interface or other hardware to enable an operator to control operation of the system 100.

In some embodiments, the invention includes using any of the methods or systems described herein to diagnose a subject with the presence or absence of a disease, disorder, condition, disease condition, or medical condition, including, but in no way limited to, back pain, one or more degenerate discs, joint pain, one or more degenerate joints or the like, based upon the images acquired.

In various embodiments, the invention teaches a system configured to perform the methods described herein, wherein the system includes a magnetic resonance imaging device (including but in no way limited to any type of magnetic resonance imaging device described herein or in any reference cited herein) operably connected to (through physical or electronic communication) a computing device. The computing device may include, but is in no way limited to, a desktop computer, a laptop computer, or handheld computing device with sufficient computing capabilities to perform the methods described herein. In some embodiments, the computing device is specifically configured to perform the steps of one or more of the methods for image analysis set forth herein.

In accordance with the present invention, a "communication link," as used in this disclosure, means a wired and/or wireless medium that conveys data or information between at least two points. The wired or wireless medium may include, for example, a metallic conductor link, a radio frequency (RF) communication link, an Infrared (IR) communication link, an optical communication link, or the like, without limitation. The RF communication link may include, for example, WiFi, WiMAX, IEEE 802.11, DECT, 0G, 1G, 2G, 3G or 4G cellular standards, Bluetooth, and the like.

Computers and computing devices typically include a variety of media, which can include computer-readable storage media and/or communications media, in which these two terms are used herein differently from one another as follows.

Computer-readable storage media can be any available storage media that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

On the other hand, communications media typically embody computer-readable instructions, data structures, program modules or other structured or unstructured data in a data signal that can be transitory such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

Stored on any one or on a combination of computer readable media, the exemplary embodiments of the present disclosure may include software for controlling the devices and subsystems of the exemplary embodiments, for driving the devices and subsystems of the exemplary embodiments, for enabling the devices and subsystems of the exemplary embodiments to interact with a human user, and the like. Such software can include, but is not limited to, device drivers, firmware, operating systems, development tools, applications software, database management software, and the like. Computer code devices of the exemplary embodiments can include any suitable interpretable or executable code mechanism, including but not limited to scripts, interpretable programs, dynamic link libraries (DLLs), Java classes and applets, complete executable programs, and the like. Moreover, processing capabilities may be distributed across multiple processors for better performance, reliability, cost, or other benefits.

To provide aspects of the present disclosure, embodiments may employ any number of programmable processing devices that execute software or stored instructions. Physical processors and/or machines employed by embodiments of the present disclosure for any processing or evaluation may include one or more networked (Internet, cloud, WAN, LAN, satellite, wired or wireless (RF, cellular, WiFi, Bluetooth, etc.)) or non-networked general purpose computer systems, microprocessors, filed programmable gate arrays (FPGAs), digital signal processors (DSPs), micro-controllers, smart devices (e.g., smart phones), computer tablets, handheld computers, and the like, programmed according to the teachings of the exemplary embodiments. In addition, the devices and subsystems of the exemplary embodiments can be implemented by the preparation of application-specific integrated circuits (ASICs) or by interconnecting an appropriate network of conventional component circuits. Thus, the exemplary embodiments are not limited to any specific combination of hardware circuitry and/or software.

Some embodiments of the present invention can be defined as any of the following numbered paragraphs:

1. A method, comprising:
   imaging a region of a subject's body with a magnetic resonance imaging (MRI) scanner; and
   measuring one or more physiological biomarkers within the imaged region, wherein (a) the physiological biomarkers comprise a labile proton ratio ($f_r$) between a solute pool and a water pool and/or an exchange rate ($k_{sw}$) between the solute pool and the water pool.

2. The method of paragraph 1, wherein the region is imaged using a chemical exchange saturation transfer (CEST) sequence.

3. The method of paragraph 1, wherein the region is imaged using a two dimension (2D) reduced field-of-view (rFOV) turbo spin echo (TSE) chemical exchange saturation transfer (CEST) sequence.

4. The method of paragraph 1, further comprising diagnosing the subject with a condition characterized by pain and/or tissue degeneration if the physiological biomarkers detected from imaging indicate one or more abnormal physiological states within the imaged region, said abnormal physiological states selected from the group consisting of low pH and/or low GAG concentration compared to a normal subject without the condition.

5. The method of paragraph 1 or 2, wherein the imaged region of the subject's body comprises a joint or an intervertebral disc.

6. The method of paragraph 2 or 3, wherein the condition is selected from the group consisting of: intervertebral disc degeneration, discogenic pain, osteoarthritis, rheumatoid arthritis, an articular cartilage injury, temporomandibular disc degeneration and combinations thereof.

7. The method of paragraph 3 or 4, further comprising determining that an origin of the subject's pain associated with the condition is within the region of the subject's body where the abnormal physiological state is detected.

8. The method of paragraph 1, wherein the MRI scanner is a 3.0 T MRI scanner.

9. The method of paragraph 1, wherein the MRI scanner is a 1.5 T MRI scanner.

10. The method of paragraph 1, wherein the MRI scanner is a 7.0 T MRI scanner.

11. The method of paragraph 1, wherein the imaging is performed by using reduced field-of-view (rFOV) excitation.

12. The method of paragraph 1, wherein a slice thickness for the MRI scan is selected to be small enough to avoid fat signal interference.

13. A non-transitory computer-readable medium having computer-readable instructions for causing one or more processors of a magnetic resonance imaging (MRI) machine to execute a method, comprising:
    applying an MRI pulse sequence to a volume of interest (VOI) in a subject, wherein the VOI comprises a joint or an intervertebral disc (IVD) or a portion thereof;

acquiring magnetic resonance data from the volume of interest (VOI) in the subject; and measuring, based on the magnetic resonance data acquired, one or more physiological biomarkers within the imaged region, wherein (a) the physiological biomarkers comprise a labile proton ratio ($f_r$) between a solute pool and a water pool and/or an exchange rate ($k_{sw}$) between the solute pool and the water pool.

14. The non-transitory computer-readable medium of paragraph 13, wherein the pulse sequence is a two dimension (2D) reduced field of view (rFOV) turbo spin echo (TSE) chemical exchange saturation transfer (CEST) sequence.

15. The non-transitory computer-readable medium of paragraph 13, wherein the MRI scanner is a 3.0 T MRI scanner.

16. The non-transitory computer-readable medium of paragraph 13, wherein the MRI scanner is a 1.5 T MRI scanner.

17. A magnetic resonance imaging system, comprising:
a magnet operable to provide a magnetic field;
a transmitter operable to transmit to a region within the magnetic field;
a receiver operable to receive a magnetic resonance signal from the region;
one or more processor operable to control the transmitter and the receiver; and
a non-transitory computer-readable medium having computer-readable instructions for causing one or more processor of the magnetic resonance imaging (MRI) system to execute a method, comprising:
applying a pulse sequence to a volume of interest (VOI) in a subject, wherein the VOI comprises a joint or an intervertebral disc (IVD) or a portion thereof;
acquiring magnetic resonance data from the volume of interest (VOI) in the subject; and
measuring, based on the magnetic resonance data acquired, one or more physiological biomarkers within the imaged region, wherein (a) the physiological biomarkers comprise a labile proton ratio ($f_r$) between a solute pool and a water pool and/or an exchange rate ($k_{sw}$) between the solute pool and the water pool.

Some embodiments of the present invention can be defined as any of the following numbered paragraphs:

1. A method for diagnosing a condition in a subject, the method comprising:
imaging a region of a subject's body with a magnetic resonance imaging (MRI) scanner, wherein the region is imaged using a quantitative chemical exchange saturation transfer (qCEST) sequence;
measuring one or more physiological biomarkers within the imaged region, wherein the physiological biomarkers comprise a labile proton exchange rate ($k_{sw}$) between a solute pool and a water pool; and
determining that the subject has the condition if the labile proton exchange rate is increased relative to a reference value.

2. The method of paragraph 1, wherein the increased labile proton exchange rate is correlated to a low pH value.

3. The method of paragraph 1, wherein the increased labile proton exchange rate is greater than 200 exchanges/second.

4. The method of paragraph 1, wherein the increased labile proton exchange rate is from 201 to 1000 exchanges/second.

5. The method of paragraph 2, wherein the low pH value is from 5.6 to 6.99.

6. The method of paragraph 1, wherein the reference value is a reference labile proton exchange rate, wherein the reference labile proton exchange rate is from 100 to 200 exchanges/second.

7. The method of paragraph 6, wherein the reference labile proton exchange rate is correlated to a reference pH value.

8. The method of paragraph 7, wherein the reference pH value is from 7.0 to 7.2.

9. The method of paragraph 1, wherein the wherein the condition is selected from intervertebral disc degeneration, discogenic pain, discogenic low back pain, chronic low back pain, low back pain, back pain, chronic back pain, progressive intervertebral disc degeneration, osteoarthritis, rheumatoid arthritis, an articular cartilage injury, temporomandibular disc degeneration and combinations thereof.

10. The method of paragraph 1, wherein the imaged region of the subject's body comprises a joint or an intervertebral disc.

11. The method of paragraph 1, wherein the condition is a painful condition.

12. The method of paragraph 1, wherein the increased labile proton exchange rate is correlated with an upregulation of one or more pain-related factors in the subject.

13. The method of paragraph 12, wherein the one or more pain-related factors are selected from bradykinin receptor B1 (BDKRB1), calcitonin gene-related peptide (CGRP), and catechol-0-methyltransferase (COMT).

14. The method of paragraph 1, wherein the increased labile proton exchange rate is correlated with an upregulation of one or more inflammation-related factors in the subject.

15. The method of paragraph 14, wherein the inflammation-related factor is interleukin-6 (IL-6).

16. The method of paragraph 1, wherein the increased labile proton exchange rate is correlated with an upregulation of one or more neurogenic factors in the subject.

17. The method of paragraph 16, wherein the neurogenic factor is brain-derived neurotrophic factor (BDNF) or nerve growth factor (NGF).

18. The method of paragraph 1, wherein the quantitative chemical exchange saturation transfer (qCEST) sequence is a two dimension (2D) quantitative chemical exchange saturation transfer (qCEST) sequence.

19. The method of paragraph 1, wherein the quantitative chemical exchange saturation transfer (qCEST) sequence is a three dimension (3D) quantitative chemical exchange saturation transfer (qCEST) sequence.

20. The method of paragraph 1, wherein the MRI scanner is a 3.0 T MRI scanner.

21. The method of paragraph 1, wherein the MRI scanner is a 1.5 T MRI scanner.

22. The method of paragraph 1, wherein the MRI scanner is a 7.0 T MRI scanner.

23. The method of paragraph 1, further comprising determining that an origin of the subject's condition is within the imaged region of the subject's body where the physiological biomarker was measured.

24. The method of paragraph 2, wherein the low pH value is indicative of the subject having the condition.

25. The method of claim 1, further comprising selecting one or more treatments for the subject if the condition is determined.

26. The method of claim 1, further comprising treating the subject with one or more treatments if the condition is determined.

Various embodiments of the present invention are described in the ensuing examples. The examples are intended to be illustrative and in no way restrictive.

Examples

The following examples are not intended to limit the scope of the claims to the invention, but are rather intended to be exemplary of certain embodiments. Any variations in the exemplified methods which occur to the skilled artisan are intended to fall within the scope of the present invention.

The invention will be further explained by the following examples, which are intended to be purely exemplary of the invention, and should not be considered as limiting the invention in any way. The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Theory

By way of additional background, previous studies have focused on the two-pool exchange model using Bloch-McConnell equations, describing the proton exchange between pool 'w' (water pool) and pool 's' (solute pool). In this two-pool system, $f_r$ refers to the labile proton ratio $M_{0s}/M_{0w}$ and $k_{sw}$ refers to the exchange rate between solute pool and water pool. $R_{1w}$, $R_{2w}$, $R_{1s}$ and $R_{2s}$ are longitudinal and transverse relaxation rates for water protons and solute protons, respectively.

The conventional CEST asymmetry analysis takes direct difference between the label scan (at the resonant frequency of the solute pool) and reference scan (at the opposite frequency with respect to water). It can be defined as $CESTR = Z_{label} - Z_{ref}$, where $Z_{label}$ and $Z_{ref}$ are the normalized signal intensity or Z-spectrum for the label scan and reference scan.

Recent studies have simplified the inverse CEST difference ($CESTR_{ind}$) as $$\frac{1}{CESTR_{ind}} = \frac{1}{\frac{1}{Z_{label}} - \frac{1}{Z_{ref}}} \approx \frac{R_{1w}}{f_r \cdot k_{sw}} + \frac{k_{sw} \cdot (R_{2s} + k_{sw}) \cdot R_{1w}}{f_r \cdot k_{sw}} \frac{1}{\omega_1^2} \quad [1]$$

where $Z_{label}$ and $Z_{ref}$ are the normalized signal intensity or Z-spectrum for the label scan (at the resonant frequency of the solute pool) and reference scan (at the opposite frequency with respect to water). $\omega_1$ is the RF irradiation amplitude.

Eq. 1 is only valid for cw CEST saturation. When pulsed saturation is applied in CEST experiments, Eq. 1 can be written as $$\frac{1}{CESTR_{ind}} \approx \frac{R_{1w}}{DC \cdot f_r \cdot k_{sw} \cdot c_1} + \frac{k_{sw} \cdot (R_{2s} + k_{sw}) \cdot R_{1w} \cdot c_2^2}{DC \cdot f_r \cdot k_{sw} \cdot c_1} \frac{1}{\omega_1^2} \quad [2]$$

where DC stands for duty cycle; $c_1$ and $c_2$ describe the shape of Gaussian saturation pulses ($c_1 = \sigma\sqrt{2\pi}/t_p$, $c_2 = c_1\sqrt{\sqrt{2}}$; $\sigma$ and $t_p$ are the width and length of the Gaussian pulse). Note $\omega_1$ here is defined as the average RF irradiation amplitude of one Gaussian pulse, i.e., $\omega_1$=flip angle/pulse duration.

In this expression, $1/CESTR_{ind}$ is described as a linear function of $1/\omega_1^2$. By measuring $CESTR_{ind}$ with different RF irradiation amplitude, the slope m and intercut n can be calculated, and eventually $k_{sw}$ and $f_r$ can be estimated.

$$k_{sw} = \frac{\sqrt[2]{R_{2s}^2 + \frac{4m}{n \cdot c_2^2}} - R_{2s}}{2} \quad [Eq. 3]$$

$$f_r = \frac{R_{1w}}{k_{sw} \cdot n \cdot c_1 \cdot DC} \quad [Eq. 4]$$

$R_{1w}$ can be measured using $T_1$ mapping techniques. $R_{2s}$ of GAG is estimated to be 200 s$^{-1}$ (See Lee J-S, Xia D, Jerschow A, Regatte R R. In vitro study of endogenous CEST agents at 3 T and 7 T. Contrast Media Mol Imaging 2016; 11:4-14. doi: 10.1002/cmmi.1652, which is hereby incorporated herein by reference in its entirety as though fully set forth).

Note Eq. 1 is a simplified expression that describes the steady state of CEST experiments. When performing qCEST experiments, RF saturation pulses need to be long enough to ensure the steady state is reached. The simplification only holds for dilute CEST agents undergoing slow and intermediate chemical exchange.

Methods

Phantom

Two sets of phantoms containing GAG prepared from chondroitin sulphate A (Aldrich-Sigma, St. Louis, Mo.) and phosphate buffer solution (PBS) with varying pH values and concentrations were prepared. For the pH set, the GAG concentration was fixed at 60 mM and pH was titrated to 5.8, 6.1, 6.4, 6.7 and 7.0. For the concentration phantom, various GAG concentrations (100 mM, 80 mM, 60 mM, 40 mM and 20 mM) were used and the pH titrated to 7.0. The solution was then transferred to 15 mL tubes. These ten tubes were put in a phantom holder filled with water.

In Vitro MRI Experiments

Imaging experiments were performed at room temperature on a 3.0 Tesla clinical scanner (Magnetom Verio; Siemens Healthcare, Erlangen, Germany). All images were acquired with a slice thickness of 8 mm, filed of view of 160×160 mm$^2$ and imaging matrix of 128×128. CEST MRI was performed with pulsed RF saturation turbo spin echo (TSE) sequence (TR/TE=16000/12 ms; 2 averages). CEST saturation module consists of 39 Gaussian-shaped pulses, with a duration $t_p$=80 ms for each pulse and an interpulse delay $t_d$=80 ms (duty cycle=50%, total saturation time Tsat=6240 ms) at saturation flip angle 900°, 1500°, 2100° and 3000° ($B_1$ amplitudes=flip angle/($\gamma t_p$)=0.73 µT, 1.22 µT, 1.71 µT and 2.45 µT; Gaussian saturation pulse parameters c1=0.50, c2=0.59). Z-spectrum was acquired with varying saturation frequencies (10 different saturation frequencies) at ±1.6 ppm, ±1.3 ppm, ±1.0 ppm, ±0.7 ppm and ±0.4 ppm. $B_0$ field was corrected using a water saturation shift referencing (WASSR) map (See Kim M, et al. Water saturation shift referencing (WASSR) for chemical exchange saturation transfer (CEST) experiments. Magnetic Resonance in Medicine 2009; 61:1441-1450. doi: 10.1002/mrm.21873, which is hereby incorporated herein by reference in its entirety as though fully set forth). $T_1$-weighted MR images were acquired by an inversion recovery TSE sequence with 10 different inversion delays (TI=50-4000 ms (i.e., TI=50, 150, 350, 700, 1050, 1400, 2000, 2500, 3000, and 4000 ms); TR/TE=6000/12 ms). $T_2$-weighted MR images were acquired by a TSE sequence with varying echo delays (TE=12-399 ms (i.e., TE=12, 24, 48, 97, 205 and 399 ms); TR=6000 ms).

Animal Preparation

All animal-related procedures were approved by the Institutional Animal Care and Use Committee (IACUC) at Cedars-Sinai Medical Center. A total of four female Yucatan minipigs (S&S Farms) were used. Following an 18-hour preoperative fast, each pig was sedated with intramuscular drugs (acepromazine 0.25 mg/kg, ketamine 20 mg/kg, and atropine 0.02-0.05 mg/kg), following which the animal was injected intravenously with propofol (2 mg/kg) to induce full anesthesia. After this had been achieved, the trachea was intubated and anesthesia was maintained using 1-3.5% isoflurane inhaled via the tracheal tube for the duration of the procedure. Following anesthesia, under fluoroscopic guidance three MR-compatible 14G coaxial needles (In vivo, Gainesville, Fla.) were inserted into the mid substance of lumbar discs L1/L2, L3/L4 and L5/L6. These lumbar discs were injected with different concentrations of Na-Lactate (Sigma Aldrich, St. Louis, Mo.) in order to induce a gradient of pH values within the discs ranging from 5-7, as described by Melkus et al, and in accordance with pH values measured within patients' pathological discs. Following intra-discal injection, exact pH values inside the discs were measured using a custom-made needle-shaped tissue pH probe (Warner Instruments, LLC, Hamden, Conn.) which was inserted through the MR-compatible needle, shortly before the MR scan. Lumbar disc L2/L3 was also scanned as the control disc. Its pH value was measured immediately after the animal was euthanized.

In Vivo MRI Experiments

Imaging experiments were performed on a 3.0 Tesla clinical scanner (Magnetom Verio; Siemens Healthcare, Erlangen, Germany). Animal was placed in right decubitus position with body array coils wrapped centered on posterior aspect spinous process. Throughout the imaging procedures, anesthesia was maintained with isoflurane (1-3.5%).

CEST MRI was performed using a two-dimension (2D) reduced filed-of-view (rFOV) TSE CEST sequence (TR/TE=10500/10 ms, 2 averages, single shot). rFOV can effectively suppress bowel motion artifacts and increase scan efficiency (see Liu Q et al. Reliable chemical exchange saturation transfer imaging of human lumbar intervertebral discs using reduced-field-of-view turbo spin echo at 3.0 T. NMR in Biomedicine 2013; 26:1672-1679. doi: 10.1002/nbm.3001, which is hereby incorporated herein by reference in its entirety as though fully set forth). For each IVD, images were acquired in the axial plane with a slice thickness of 3 mm, filed of view of 100×40 $mm^2$ and spatial resolution of 0.8×0.8 $mm^2$. CEST saturation module consists of 39 Gaussian-shaped pulses, with a duration $t_p$=80 ms for each pulse and an interpulse delay $t_d$=80 ms (duty cycle=50%, total saturation duration $T_s$=6240 ms) at saturation flip angle 900°, 1500°, 2100° and 3000° ($B_1$ amplitudes=flip angle/$(\gamma t_p)$=0.73 µT, 1.22 µT, 1.71 µT and 2.45 µT; Gaussian saturation pulse parameters c1=0.50, c2=0.59). Z-spectrum was acquired with varying saturation frequencies (10 different saturation frequencies) at ±1.6 ppm, ±1.3 ppm, ±1.0 ppm, ±0.7 ppm and ±0.4 ppm. Scan time of the CEST experiment for each RF irradiation amplitude is ~6 min. $B_0$ field was corrected using WASSR.

$T_1$-weighted MR images were acquired by an inversion recovery TSE sequence with 7 varying TI (50 ms, 150 ms, 350 ms, 700 ms, 1050 ms, 1400 ms and 2000 ms). Images were acquired at the same slice position as the CEST MRI sequence (TR/TE=6000/12 ms; 1 average; FOV=200×200 $mm^2$; spatial resolution=0.8×0.8×3 $mm^3$; scan time=~2.5 min).

Data Analysis

Post processing was performed with custom-written programs in Matlab (The Mathworks, Natick, Mass., USA). $CESTR_{ind}$ was calculated according to Eq. 1 after $B_0$ correction at 1.0 ppm ($Z_{lab}$=Z(+1.0 ppm), $Z_{ref}$=Z(-1.0 ppm)). Linear regression was used to perform Ω-plot analysis between $1/CESTR_{ind}$ and $1/\omega_1^2$ to obtain the slope and intercut. The exchange rate $k_{sw}$ and labile proton ratio $f_r$ were calculated afterwards following Eqs. [3] and [4]. These calculations were performed pixel-by-pixel and by region of interest (ROI). The $T_1$ maps and $T_2$ maps were obtained by pixel-by-pixel logarithmic fit of the signal equation $I=I_0[1-(1+\eta)\cdot\exp(-TI/T_1)]$ where I is the signal intensity, TI is the inversion time and η is the inversion efficiency. The $T_2$ maps were obtained by fitting the signal equation $I=I_0\cdot\exp(-TE/T_2)$ where I is the signal intensity and TE is the echo time.

Results

Phantom

Figure 1B:
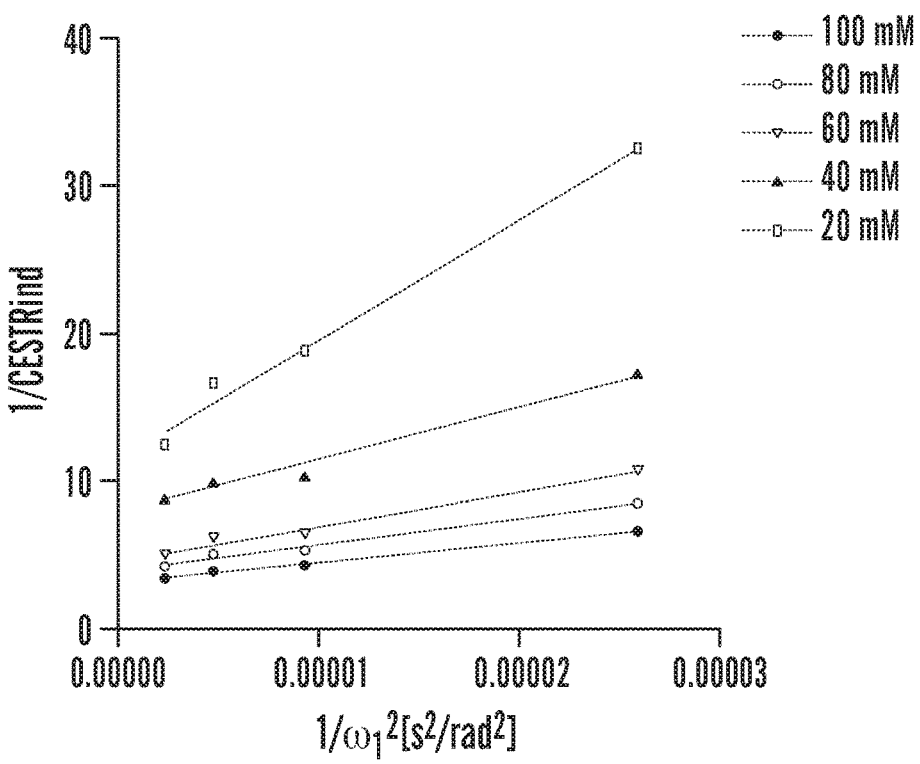

In FIG. 1, the relationship between $1/CESTR_{ind}$ and $1/\omega_1^2$ were evaluated in tubes with varying GAG concentration and pH values. $1/CESTR_{ind}$ is the average signal within the region-of-interest (ROI) of each tube. In all tubes, $1/CESTR_{ind}$ can be represented as a linear function of $1/\omega_1^2$. This experimental finding is consistent with Eq. [2].

Figure 2B:
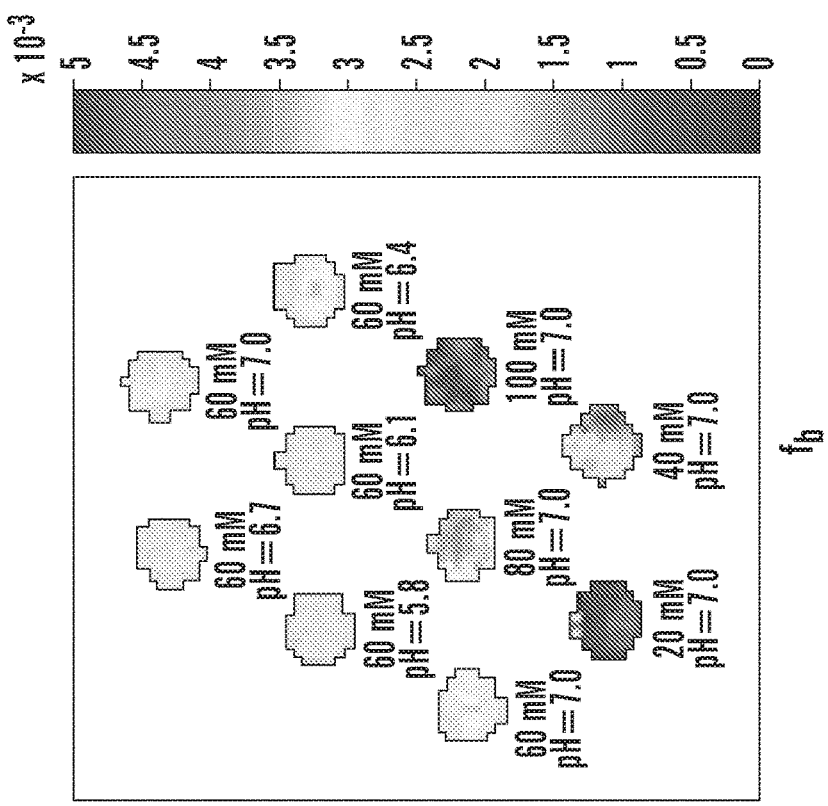
FIG. 2A-FIG. 2D depict in accordance with various embodiments of the invention, quantitative results of the phantom study.
Figure 2A:
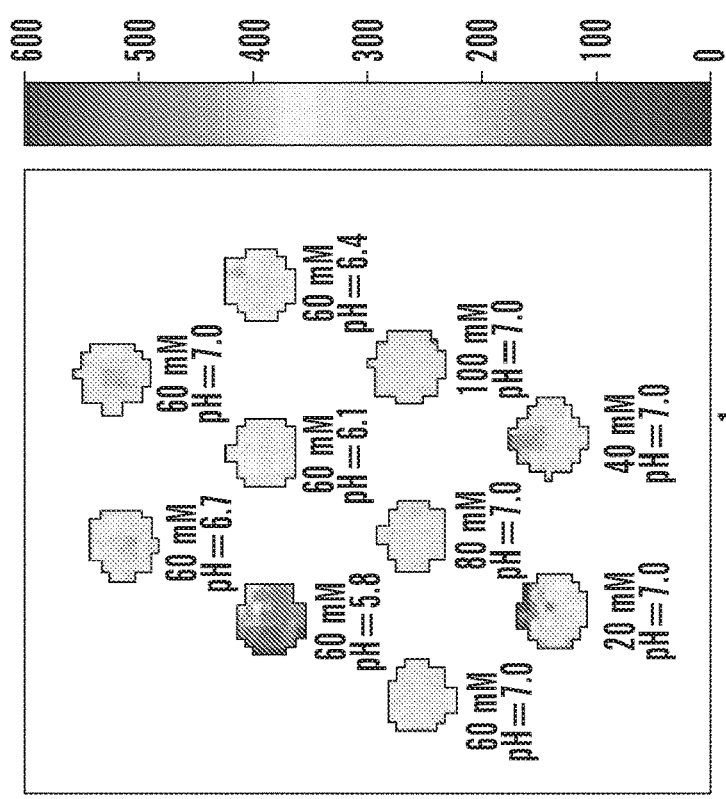
Figure 2C:
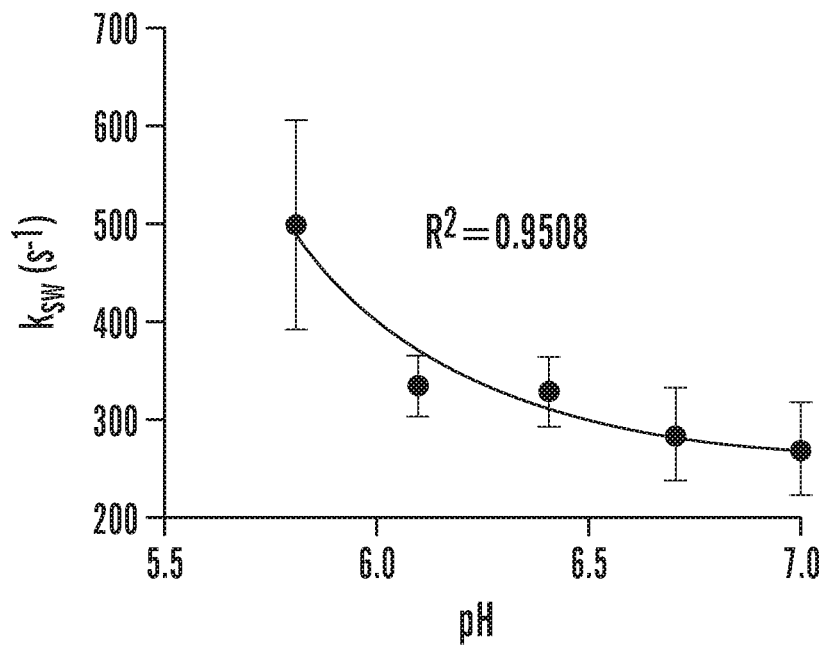
Figure 2D:
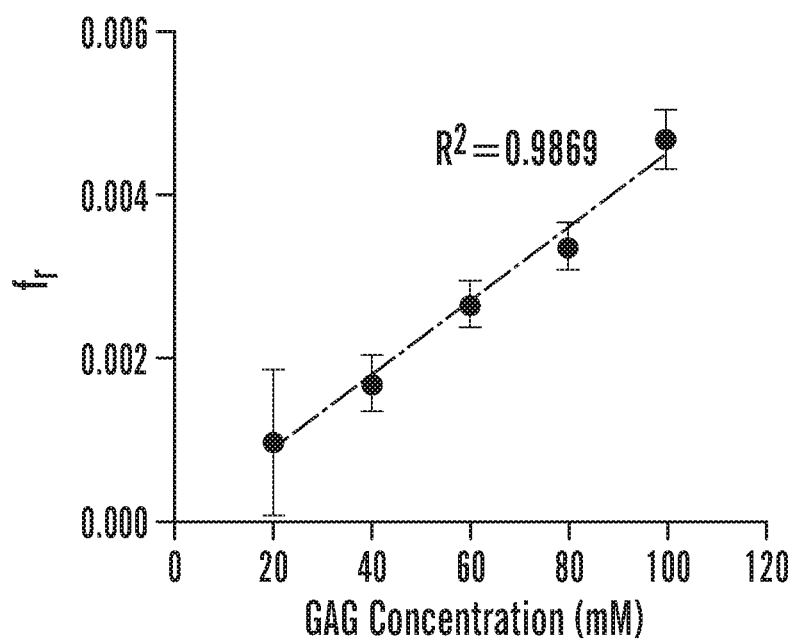

In addition, pixel-wise mapping of chemical exchange rate $k_{sw}$ and labile proton ratio $f_r$ were reconstructed, shown in FIG. 2A-FIG. 2B. It can be seen how chemical exchange rates change as pH values vary (FIG. 2A) and how labile proton ratios change as GAG concentrations vary (FIG. 2B). Quantitatively, the chemical exchange rate can be described as $k_{sw}=1.5\times10^{-pH+8}+252.0$, $R^2$=0.9508 (FIG. 2C). This follows an acid catalyzed chemical exchange formula (See Englander S W, et al. Hydrogen exchange. Annu. Rev. Biochem. 1972; 41:903-924. doi: 10.1146/annurev.bi.41.070172.004351, which is hereby incorporated herein by reference in its entirety as though fully set forth). The labile proton ratio is linearly correlated with GAG concentration (FIG. 2D). It can be represented as $f_r$=4.6× $10^{-5}$[GAG]−4.4×$10^{-5}$ ($R^2$=0.9869), where [GAG] is the GAG concentration in mM. The error bars in FIGS. 2c and 2d represent the standard deviation of all the pixels within the ROI of each tube for $k_{sw}$ and $f_r$, respectively. These experimental results encouraged in vivo application of qCEST technique.

Animal Studies

16 IVDs were studied in this work, 3 of which were excluded because the needle went through both sides of the IVD and caused morphological damage. The pH values of the studied IVDs after Na-Lactate injection ranged from 5.0 to 7.2. FIG. 3A-FIG. 3C shows the anatomical images of one representative mini-pig's lumbar IVDs and the corresponding exchange rate maps. As shown in FIG. 3A-FIG. 3C, the exchange rate was higher in the IVDs with lower pH values. Within each disc, there was some inhomogeneity in the exchange rate map. This is because the current SNR cannot guarantee accurate measurement for a signal pixel. However, the average value of each IVD proved to be more reliable. This is because SNR will increase after averaging all pixels that are in the similar pH environment.

Figure 4A:
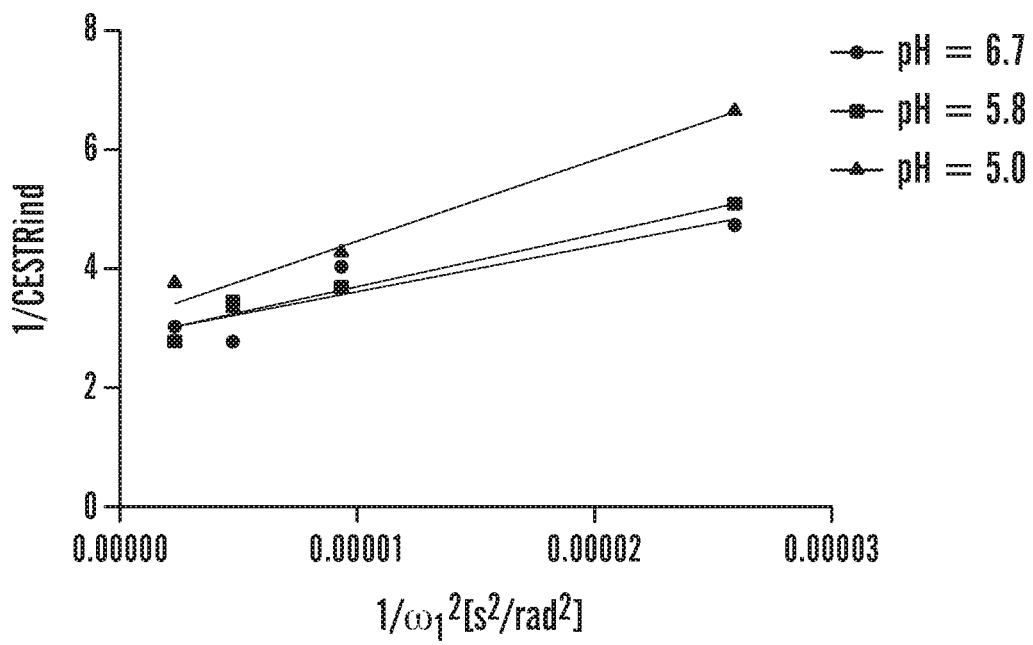
FIG. 4A-FIG. 4B depicts in accordance with various embodiments of the invention, (FIG. 4A) Ω-plots analysis of representative IVDs with varying pH values (5.0, 5.8 and 6.7) and (FIG. 4B) the chemical exchange rate as a function of pH in the animal studies.
Figure 4B:
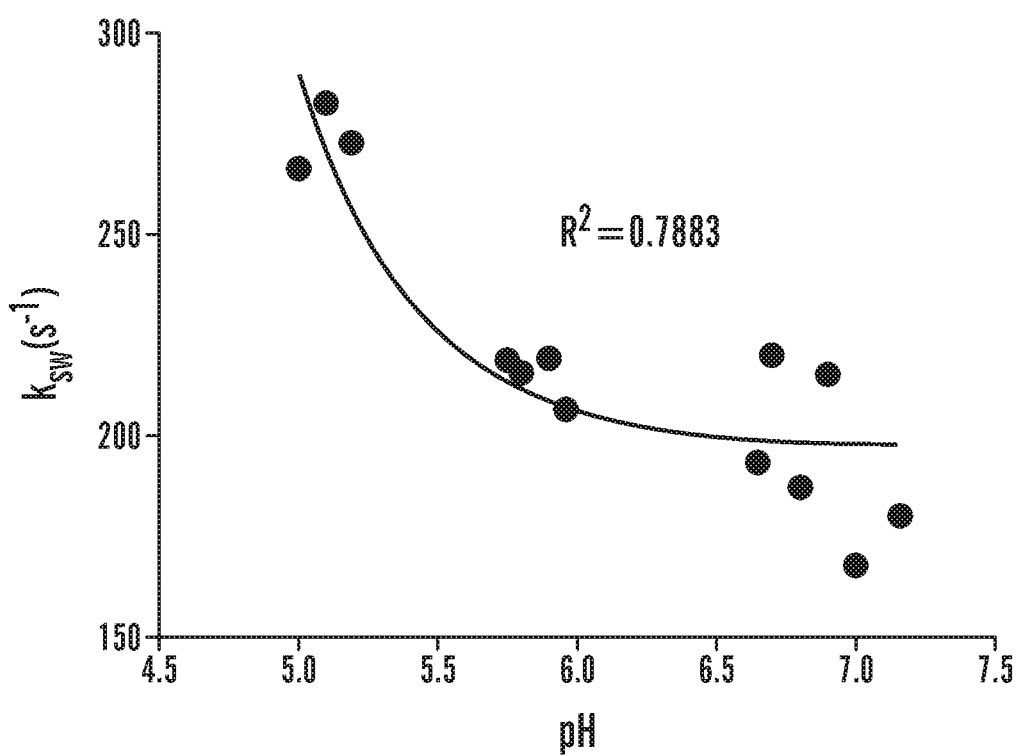

In FIG. 4A, we evaluated the relationship between $1/CESTR_{ind}$ and $1/\omega_1^2$ in representative IVDs with different pH values (5.0, 5.8 and 6.7). Similar as shown in phantom studies, $1/CESTR_{ind}$ can be represented as a linear function of $1/\omega_1^2$. In FIG. 4B, the average exchange rate of each disc was taken, and its relationship evaluated with the corresponding pH value, which was obtained by directly measuring the intra-discal pH value using a pH probe. The exchange rate can be described by an acid catalyzed chemical exchange formula, $k_{sw}=9.2\times10^{-pH+6}+196.9$, $R^2=0.7883$.

DISCUSSION

In this study, it was investigated whether qCEST analysis can be used to detect pH changes in IVDs in vivo on a 3.0 Tesla MR scanner. The phantom studies showed that the approximations used in qCEST analysis still holds true for molecules like GAG and the exchange rate determined from qCEST analysis is dependent on pH levels of GAG solutions. The relationship between the exchange rate and pH values was further studied in the in vivo porcine spine studies. The results showed the exchange rate can be described as a function of pH using acid catalyzed proton chemical exchange formula. This is believed to be the first in vivo study to show the validity of qCEST analysis using tissue pH meter as reference.

Previous studies have investigated the pH dependence of gagCEST. Even though the GAG concentration can be corrected using $T_{1\rho}$, water relaxation parameters $T_1$ and $T_2$ still contribute to the gagCEST signal. qCEST analysis, on the other hand, has been shown to detect pH changes independent of $T_1$, $T_2$ and concentration in numerical simulations and in phantom studies. It is a more reliable approach to measure pH changes in the IVD, because $T_1$ and $T_2$ change significantly after disc degeneration. In this in vivo study, a relationship was established between exchange rates and pH levels, which can be potentially applied in future studies to translate exchange rates to pH levels.

Pulsed CEST saturation pulses were used because this study was performed on a 3.0 Tesla clinical MR scanner. Pulsed qCEST analysis is even more complicated because of the constant changing RF irradiation amplitude. Pulsed CEST experiments normally report the irradiation power as the equivalent cw $B_1$ field strength. However, the proton exchange in pulsed CEST experiments is rather complicated. Simply integrating the equivalent cw $B_1$ field strength will cause errors in estimating the exchange rate and labile proton ratio. Meissner et al. came up with an analytical solution for pulsed CEST experiment (See Meissner J-E, et al. Quantitative pulsed CEST-MRI using Ω-plots. NMR in Biomedicine 2015; 28:1196-1208. doi: 10.1002/nbm.3362, which is hereby incorporated herein by reference in its entirety as though fully set forth). This enables more accurate quantitative results of pulsed CEST experiments.

In this study, the relationship between exchange rates and pH levels were explored in both phantom studies and in vivo animal studies. However, the results are not exactly the same. One reason is these two studies were performed at different temperatures (~20° C. for phantom studies and ~38° C. for animal studies). Another possible reason is GAG in the IVD experiences a more complicated environment. In addition to CEST effects, magnetization transfer (MT) effects are also present in the IVD from semi-solid components such as macromolecules, which could affect the qCEST analysis.

Regular CEST experiments are relatively slow, because of long TR, multiple averages, etc. In addition to that, qCEST analysis also requires (a) long RF saturation time (6 s in the present study) to achieve the steady state and (b) multiple CEST experiments with varying RF irradiation amplitudes to perform the Ω-plots. Compressed sensing and parallel imaging techniques can be utilized to accelerate qCEST experiments (See Heo H Y, Zhang Y, Lee D H, Jiang S, Zhao X, Zhou J. Accelerating chemical exchange saturation transfer (CEST) MRI by combining compressed sensing and sensitivity encoding techniques. Magnetic Resonance in Medicine 2016:n/a-n/a. doi: 10.1002/mrm.26141, which is hereby incorporated herein by reference in its entirety as though fully set forth), and therefore the implementation of those techniques in conjunction with the inventive systems and methods are contemplated as within the scope of the present invention.

The manipulation of pH levels in the IVDs by injecting Na-Lactate mimics the degeneration condition only to a limited extent. In addition to pH change, disc degeneration is also correlated with a loss of GAG and water content in the nucleus pulposus. GAG loss will significantly lower the CEST values and the dehydration process will cause the change of MR relaxation parameters.

Conclusion

The experiments reported in the present application demonstrate the feasibility of in vivo qCEST analysis of GAG in IVDs. The experiments reported in the present application also demonstrate that the exchange rate determined from qCEST analysis is closely correlated with pH value, and can be used to non-invasively measure pH in IVDs. qCEST technique has the potential to provide additional information on IVD physiology and help gain insight into the pathogenesis of low back pain and its underlying degenerative processes.

Example 2

Results
Induction of IVD Degeneration

Figure 6:
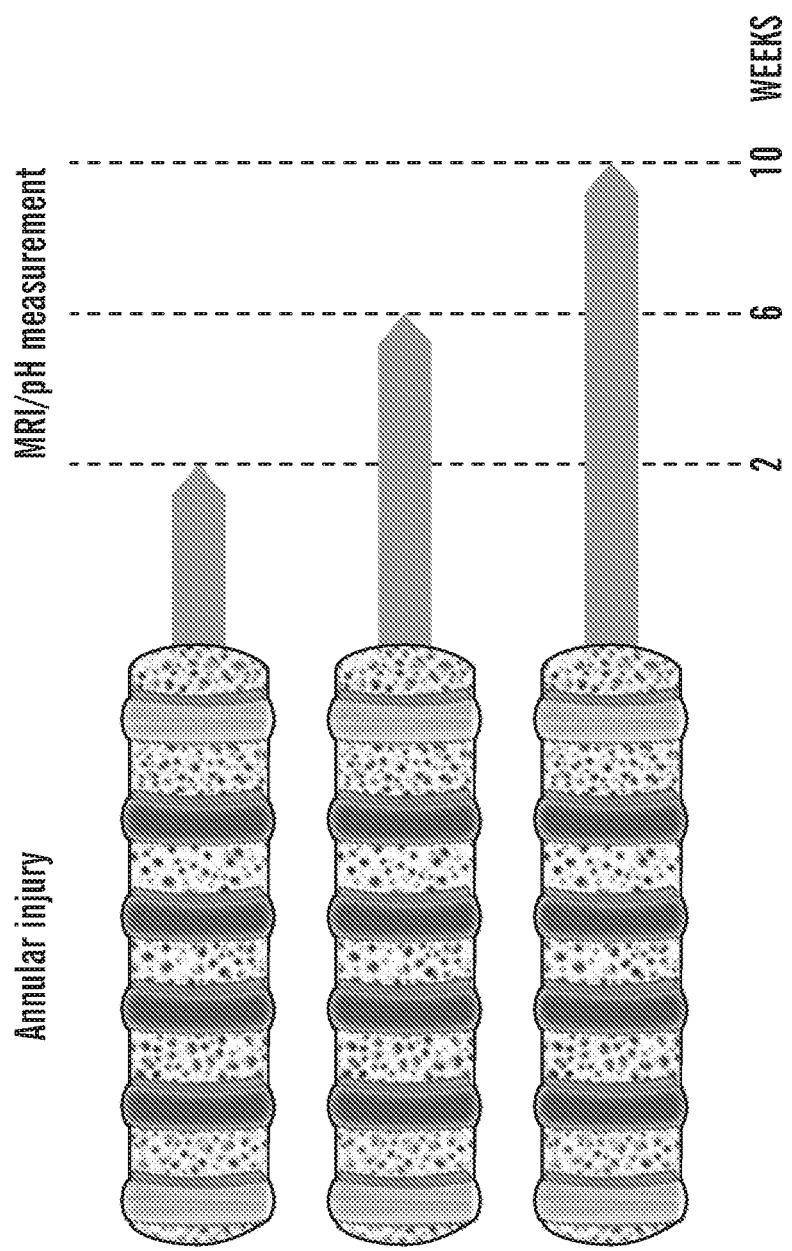
FIG. 6 depicts in accordance with various embodiments of the invention, IVD degeneration timeline. Minipigs underwent annular injury in four IVD levels to induce degeneration. Following degeneration, animals were randomly divided into 3 groups and scanned at 2, 6 and 10 weeks. At each time point, one of the groups was sacrificed and the pH within the injured IVDs was measured. The IVDs were harvested for gene analyses and histology
Figure 7A:
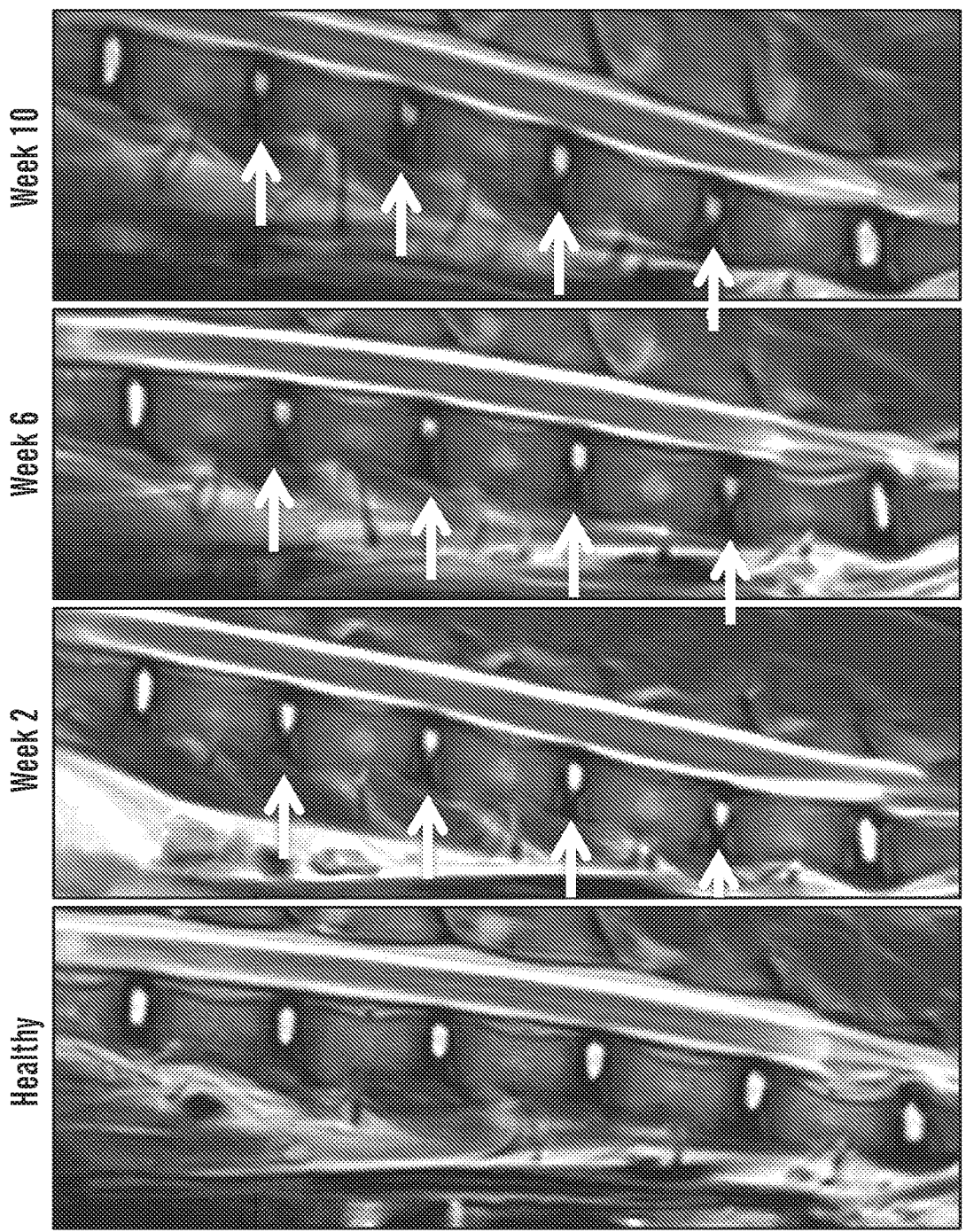
FIG. 7A-FIG. 7E depict in accordance with various embodiments of the invention, IVD degeneration following intra-discal puncture.
Figure 7D:
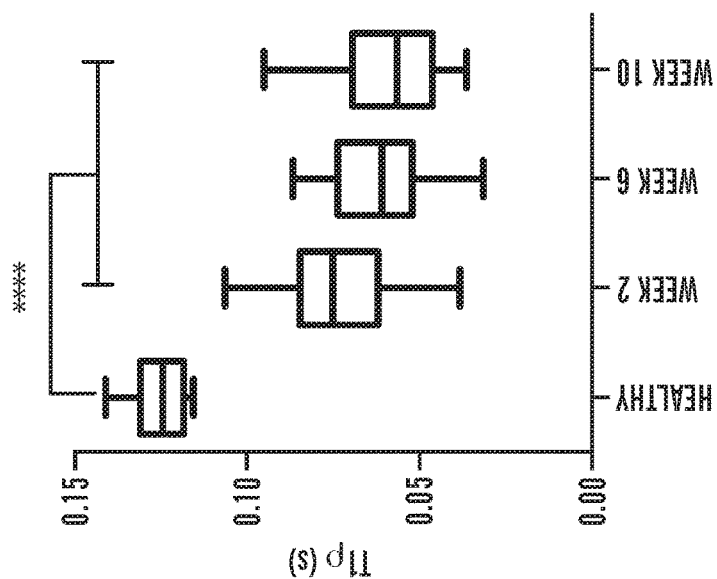
Figure 7C:
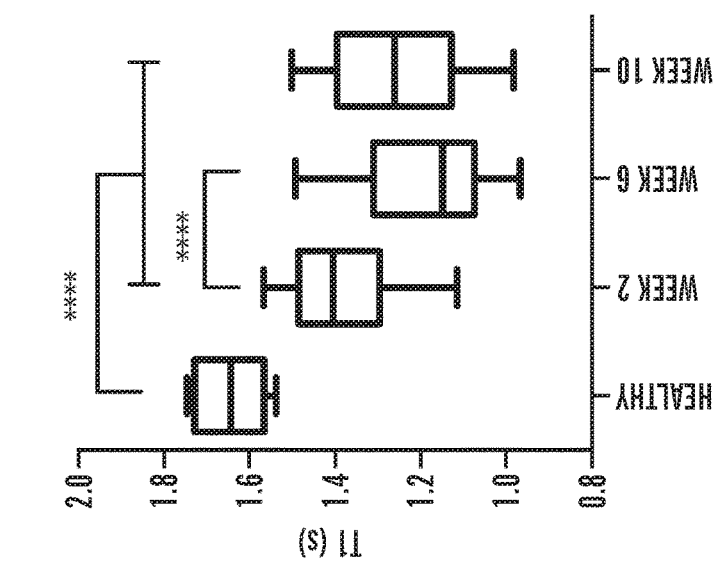
Figure 7B:
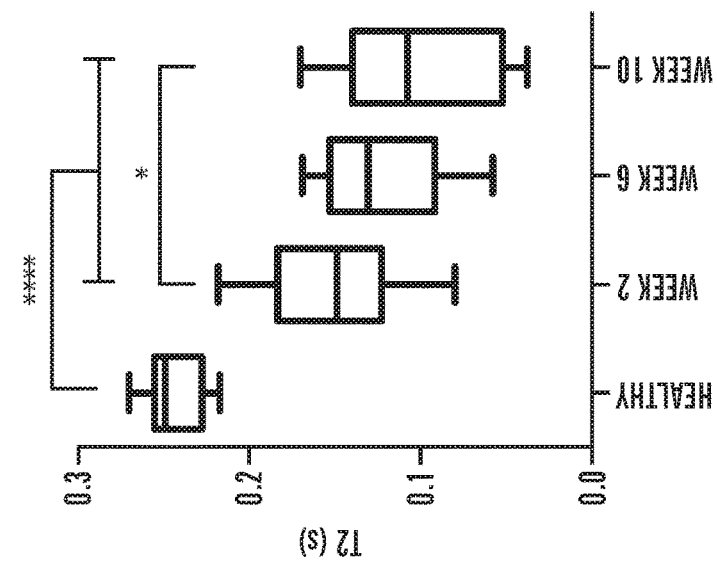
Figure 7E:
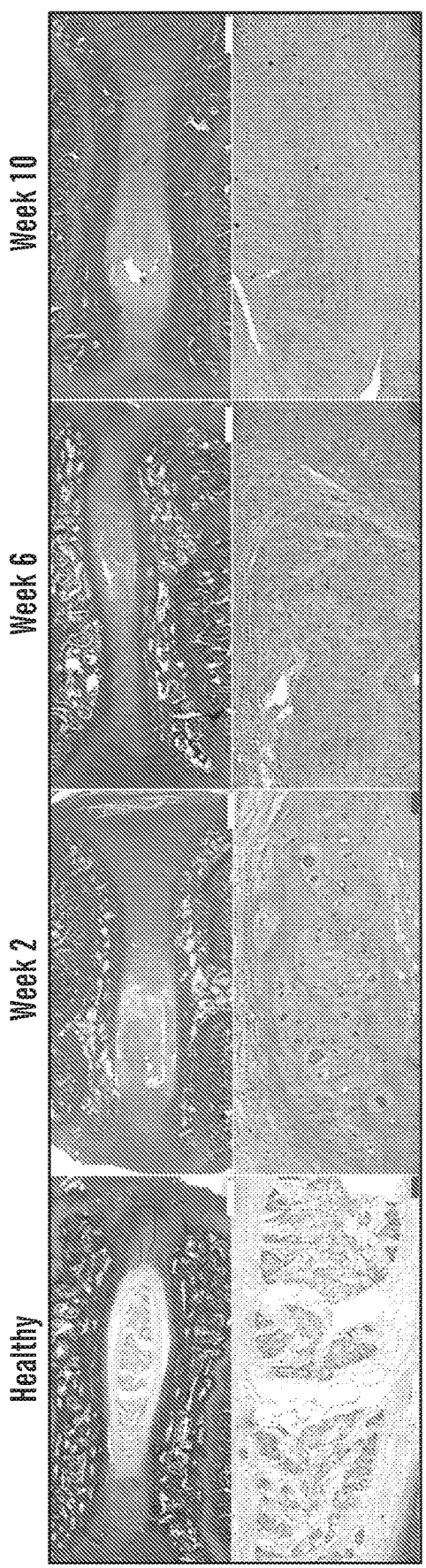

Minipigs underwent surgery during which the annulus fibrosus of four IVDs (L1/2-L4/5) were punctured to induce degeneration (FIG. 6). The progress of IVD degeneration was monitored using MRI, with a clear decrease in the intensity of the $T_2$-weighted signal in punctured IVDs compared to healthy IVDs (FIG. 7A). A two-fold decrease in water content within the punctured IVDs was evident as soon as 2 weeks after induction of degeneration compared to healthy porcine IVDs based on $T_2$-weighted mappings ($p<0.0001$; FIG. 7B). The water content was further reduced 10 weeks after induction of degeneration compared to week 2 ($p<0.05$). In addition, a significant reduction of $T_1$ signal from 1.6 to 1.4 was noticeable at 2 weeks after induction of degeneration compared to healthy controls ($p<0.0001$; FIG. 7C). Further reduction of $T_1$ signal to 1.2 was measured 6 weeks after induction of degeneration ($p<0.0001$). $T_{1\rho}$ mapping revealed two-fold reduction in signal as soon as 2 weeks after induction of degeneration ($p<0.0001$; FIG. 7D). Overall, these quantitative signals show the rapidly progressive degenerative status of the punctured IVDs. Histology revealed an abnormal IVD structure and cell matrix following puncture, with extensive fibrosis and formation of cell clusters in the nucleus pulposus, typical of degenerated IVDs (FIG. 7E).

MR Signal Correlates with Intra-Discal pH in Degenerated IVDs

Figure 8D:
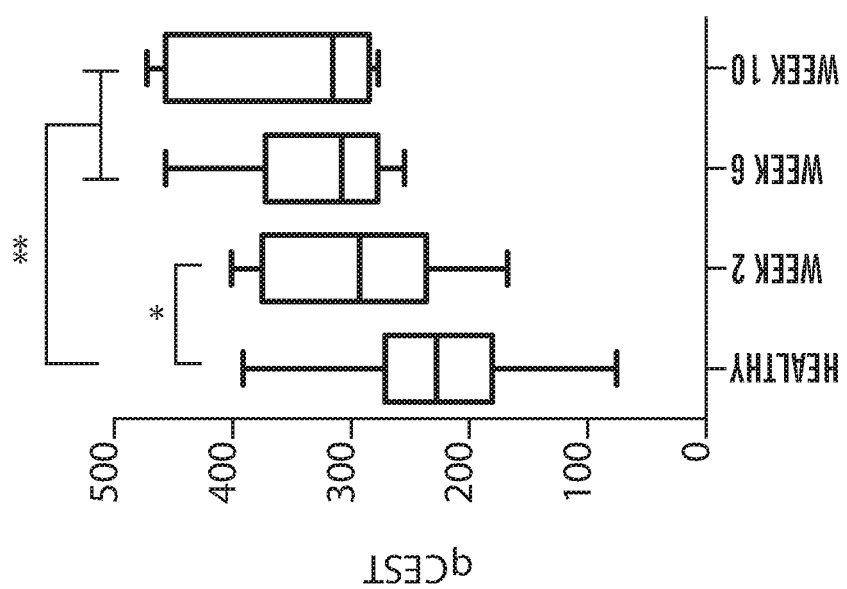
Figure 8C:
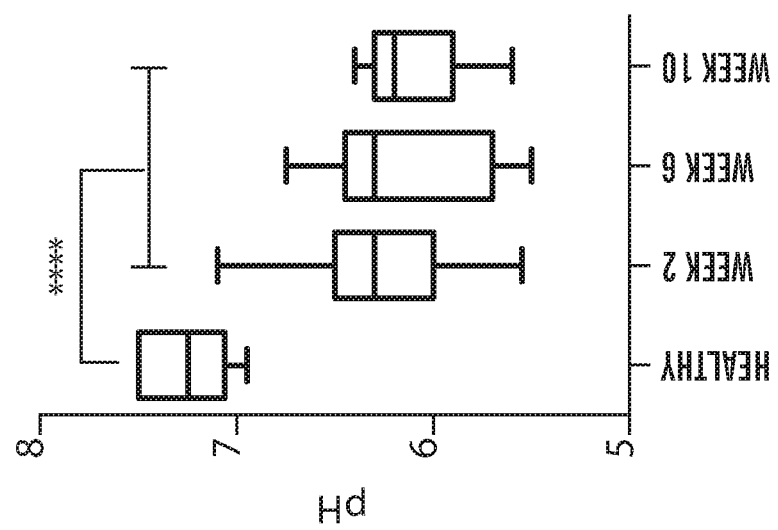

In addition to measuring the degenerative status of the IVDs, qCEST signals were acquired from the degenerative IVDs. These values were correlated to their correspondent pH readings that were measured directly from the IVDs (FIG. 8A). Strong correlation was observed between the qCEST signal and pH of the degenerated IVDs ($R^2=0.8004$; $p<0.0001$). The available qCEST readings at weeks 2, 6 and 10 were classified as either healthy or degenerated and used to create an ROC curve (area under the curve=0.813, p=0.0003) with 81.3% sensitivity and 76.1% specificity (FIG. 8B). Significant pH drop from 7.2 to 6.3 was measured in IVDs as soon as 2 weeks after injury (p=0.0001, FIG. 8C). This reduction in pH was maintained until week 10. In accordance with the pH drop, the acquired qCEST signal significantly increased 2 weeks after injury (p<0.05, FIG. 8D). Further increase in signal was observed at 6 and 10 weeks (p<0.01), demonstrating high sensitivity of the MR protocol to small changes in pH that were not statistically significant by physical measurements.

MR Signal Correlates with Pain-Markers in Degenerated IVDs

Figure 9A:
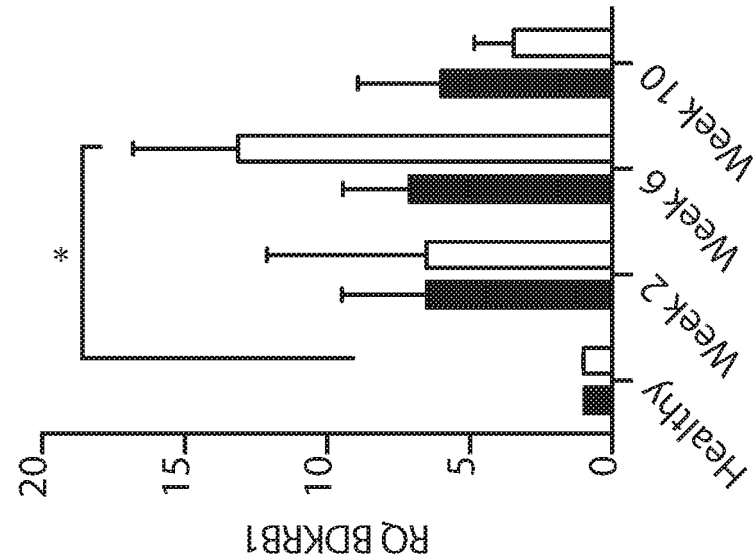
FIG. 9A-FIG. 9E depict in accordance with various embodiments of the invention, Pain and inflammatory markers upregulation in degenerating IVDs. Quantitative RT-PCR analysis of (FIG. 9A-FIG. 9C) pain-related genes (CGRP, BDKRB1 and COMT), (FIG. 9D) IL-6 and (FIG. 9E) BDNF harvested from the annulus fibrosus and nucleus pulposus of degenerated IVDs at 2, 6 and 10 weeks after induction of degeneration. (n=3 per group; *p<0.05, **p<0.01; CGRP=calcitonin gene-related peptide, BDKRB1=Bradykinin receptor B1, COMT=catechol-0-methyltransferase, BDNF=brain-derived neurotrophic factor).
Figure 9B:
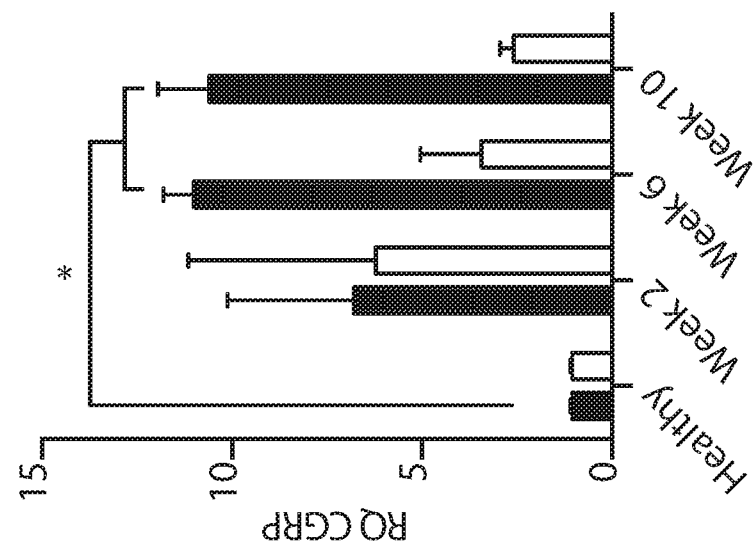
Figures 9C, 9D:
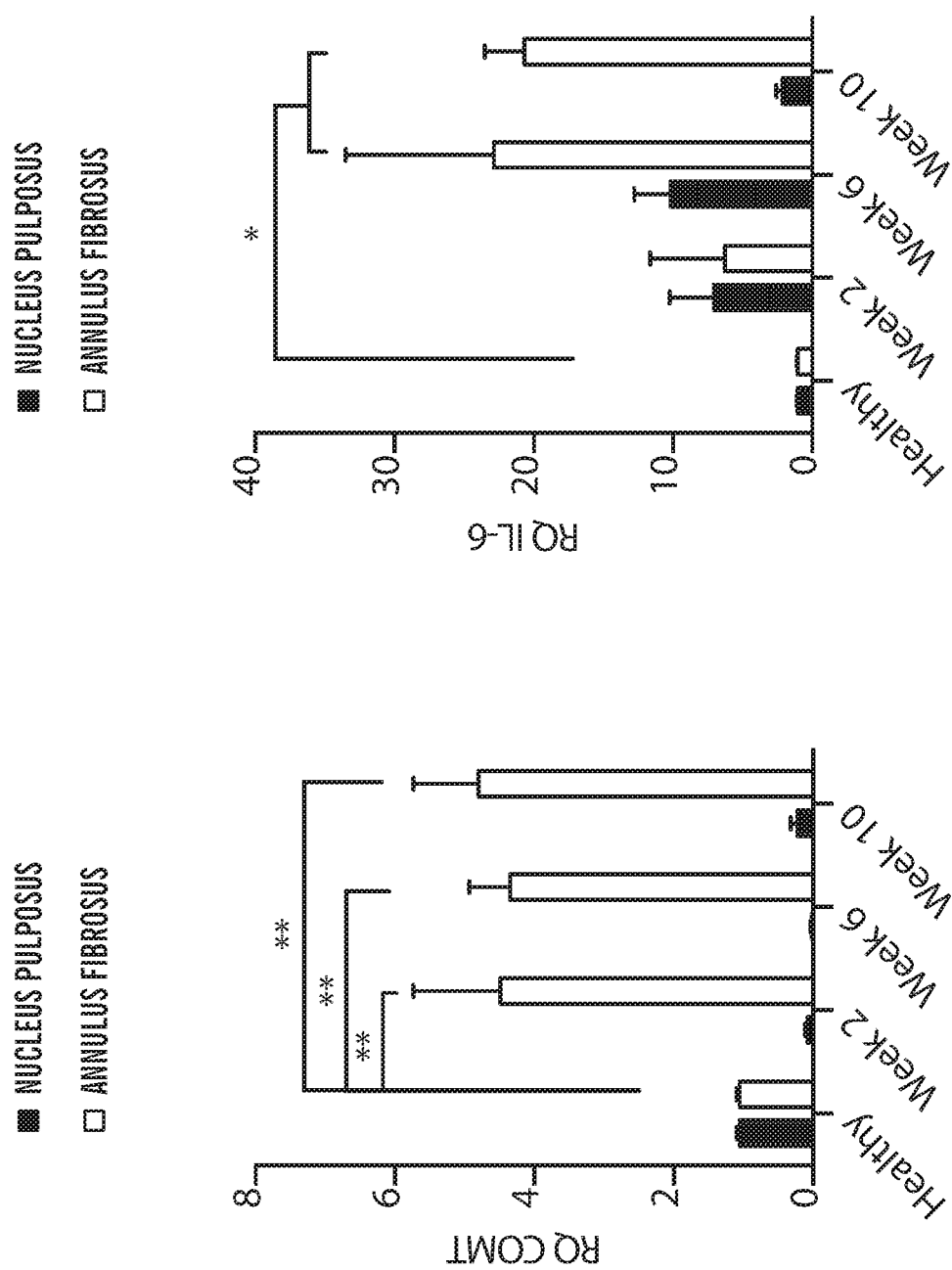
Figure 9E:
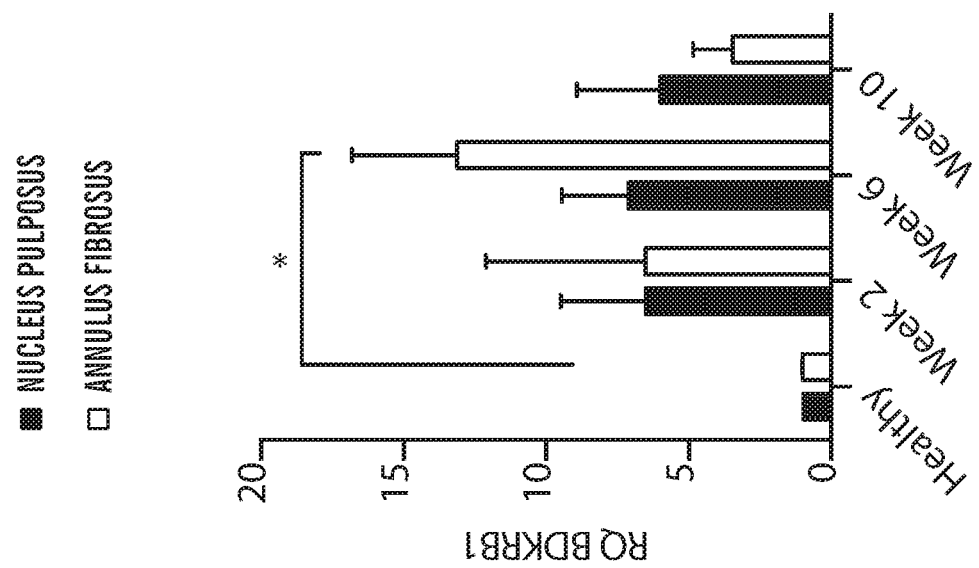
Figure 10:
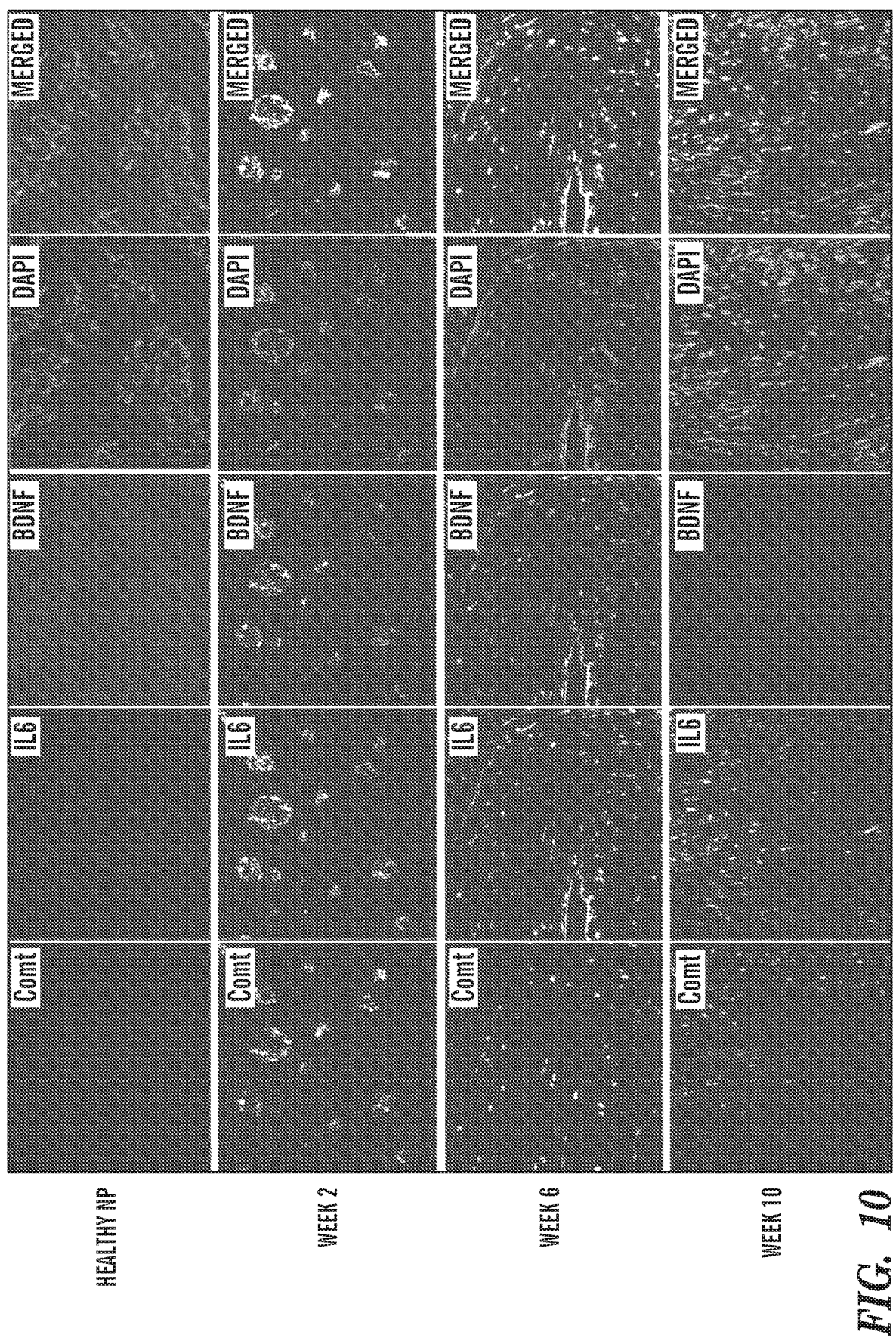
FIG. 10 depicts in accordance with various embodiments of the invention, Immunofluorescence analysis of IVD degeneration and marker upregulation. Immunostaining of serial slides of nucleus pulposus from weeks 2, 6 and 10 after degeneration against COMT, IL-6, BDNF, CGRP, BDKRB1 and counterstaining with DAPI. Merged panels of the different stainings are presented on the right column. (NP=nucleus pulposus, CGRP=calcitonin gene-related peptide, BDKRB1=Bradykinin receptor B1, COMT=catechol-0-methyltransferase, BDNF=brain-derived neurotrophic factor)
Figure 10:
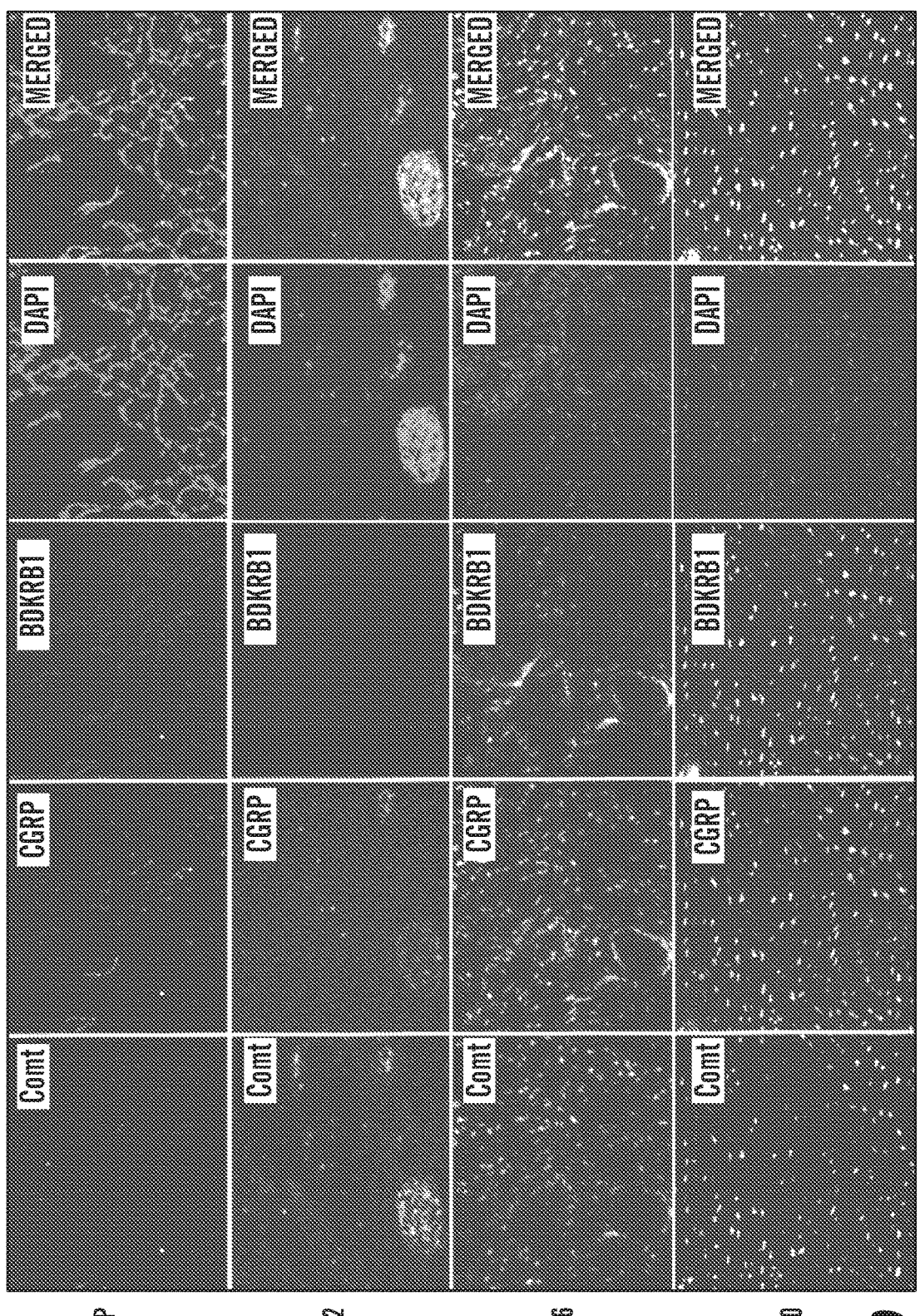

Next, we evaluated the expression of pain-related factors in the degenerated IVDs. Harvested degenerated IVDs underwent gene expression analysis of RNA that was extracted from the nucleus pulposus and annulus fibrosus. Specifically, we evaluated the expression of bradykinin receptor B1 (BDKRB1), calcitonin gene-related peptide (CGRP) and catechol-0-methyltransferase (COMT). A 10-fold increase in CGRP expression was observed in the nucleus pulposus 6 and 10 weeks after degeneration (p<0.05, FIG. 9A). A 13-fold increase in BDKRB1 expression was observed in the annulus fibrosus 6 weeks after degeneration (p<0.05), while a non-significant decrease was observed 10 weeks after degeneration (p=0.1367, FIG. 9B). There was a 4-fold increase in COMT expression in the annulus fibrosus at 2, 6 and 10 weeks after degeneration (p<0.01, FIG. 9C). In addition, expression of IL-6, which is involved with inflammatory processes, were also assessed following degeneration. IL-6 expression analysis revealed 20-fold increase in the annulus fibrosus at 6 and 10 weeks after degeneration (p<0.05, FIG. 9D). We also evaluated the expression of brain-derived neurotrophic factor (BDNF), which is involved with nerve growth. A 22-fold increase in BDNF expression in the annulus fibrosus was observed at 6 weeks after degeneration (p<0.05, FIG. 9E). Surprisingly, a non-significant downregulation was observed in the annulus fibrosus 10 weeks after degeneration (p=0.0925), while a significant 18-fold increase was observed in the nucleus pulpusos during that time (p<0.05). Immunofluorescent staining of the nucleus pulposus with antibodies against the aforementioned markers revealed increased signals and co-localizations of the studied pain markers compared to healthy IVDs (FIG. 10). Co-localization of COMT and IL-6 was observed within the degenerated IVDs, linking these processes as part of the degenerative progression. In contrast to the gene analysis results, no expression of BDNF was observed in the nucleus pulposus 10 weeks after degeneration. However, in some cases protein expression is not measurable in immunofluorescent stainings, and gene expression studies are generally more sensitive. Overall, we found that there is upregulation of several pain, inflammatory and neurogenic factors in the degenerated IVDs. Finally, the measured qCEST signals were paired with the expression levels of the aforementioned markers derived from the same IVDs, resulting in strong linear correlations (p<0.0001 for all pairings; FIG. 11A-FIG. 11E). Combined with our other results described herein, this data demonstrates that an increase in qCEST signal is correlated with an upregulation of several pain markers within the IVDs, and therefore enables detection of painful IVDs.

Discussion

Previous studies have attempted to evaluate pH as a measure for diagnosing discogenic low back pain. Zuo et al. demonstrated the feasibility of acquiring localized $^1$H spectra on a 3.0 T scanner on intact bovine and human cadaveric IVDs to quantify lactate, which causes low pH (J. Zuo, E. Saadat, A. Romero, K. Loo, X. Li, T. M. Link, J. Kurhanewicz, S. Majumdar, Assessment of intervertebral disc degeneration with magnetic resonance single-voxel spectroscopy. *Magn Reson Med* 62, 1140-1146 (2009). However, translating this technique to in vivo spectroscopy suffers from several limitations. As stated by the authors, it is difficult to differentiate lactate from the lipid peaks, because their resonance frequencies are close. Another limitation is inadequate quantification of metabolites in IVDs within the collapsed space. A later study from the same group characterized IVD in vivo by spectroscopy (J. Zuo, G. B. Joseph, X. Li, T. M. Link, S. S. Hu, S. H. Berven, J. Kurhanewicz, S. Majumdar, In vivo intervertebral disc characterization using magnetic resonance spectroscopy and T1rho imaging: association with discography and Oswestry Disability Index and Short Form-36 Health Survey. *Spine* (*Phila Pa.* 1976) 37, 214-221 (2012)). A significant elevated water/proteoglycan area ratio was found in IVDs with positive discography. In vivo MRS is challenging because of low SNR, physiological motion, and bone susceptibility induced line broadening, making the assessment of lactate imprecise.

Another study found a non-linear dependence of the CEST effect of GAG on pH in porcine IVD specimens (G. Melkus, M. Grabau, D. C. Karampinos, S. Majumdar, Ex vivo porcine model to measure pH dependence of chemical exchange saturation transfer effect of glycosaminoglycan in the intervertebral disc. *Magn Reson Med* 71, 1743-1749 (2014)). However, the study was performed ex vivo at 7.0 T MRI and the effectiveness of the method on clinical MR systems (1.5 or 3.0 T) has not been shown.

In contrast to previous studies, in this study, we used MRI to detect discogenic low back pain in vivo in a minipig model of IVD degeneration. We showed that degeneration was achieved by 10 weeks following injury, as detected by MRI and histology. A significant pH drop was observed during the degenerative process, as well as a significant increase in the qCEST signal. These changes were detected as early as 2 weeks after injury. qCEST signals were well-correlated with pH measurements obtained directly from the degenerated IVDs. Gene analysis revealed upregulation of several pain markers in degenerated IVDs, and this upregulation was strongly correlated to the increase in qCEST signal at various time points.

As such, in various embodiments, the present invention can be implemented on clinical MRI systems. qCEST technique can be used to provide additional information on IVD physiology and detect pH changes associated with early degeneration, and thus provide early diagnosis to patients. In various embodiments, the present invention also allows for earlier interventions for IVD degeneration and prevention of chronic low back pain.

Materials and Methods

Study Design

The objective of our study was to develop a pH-level dependent MR imaging approach to diagnose low back pain. Our pre-specified hypothesis was that pain in the degenerating IVDs is caused at least partially due to an intra-discal acidic environment, and this pH drop can be detected non-invasively using qCEST imaging. Nine healthy female skeletally mature Yucatan minipigs (S&S Farms; Average age 1.5 years, 35-40 kg) were included in this study. The sample size used was estimated to achieve a power of 0.8 and α=0.05 using one-way ANOVA. qCEST was investigated for its capacity to detect any pH changes within the IVDs, and see whether this change can be correlated to pain marker upregulation. For this purpose, we created an IVD degeneration model in a large, clinically-relevant animal model by puncturing the annulus fibrosus with a 14 G needle, thus creating four degenerating IVDs per minipig (FIG. 6). Then, the minipigs went through MRI scan at 2, 6 and 10 weeks after degeneration. At each time-point, three pigs were randomly euthanized in order to directly measure the pH within the IVD using pH meter, and the degenerated IVDs were harvested for gene expression analysis, histology and immunofluorescence. IVD degeneration was evaluated using imaging parameters and histology. Pain was detected using gene expression and immunofluorescence, and was compared qCEST measurements within the IVDs. Animals that developed acute procedural complications such as nerve damage or signs of distress during follow-up that compromised animal welfare were eliminated from the study.

IVD Degeneration Animal Model

All animal procedures were approved by the Cedars-Sinai Medical Center institutional review board for animal experiments. The IVD degeneration model was created with modifications from a previously established method (O. Mizrahi, D. Sheyn, W. Tawackoli, S. Ben-David, S. Su, N. Li, A. Oh, H. Bae, D. Gazit, Z. Gazit, Nucleus pulposus degeneration alters properties of resident progenitor cells. *Spine J* 13, 803-814 (2013)). Following an 18-hour preoperative fast, each minipig was sedated using intramuscular acepromazine (0.25 mg/kg), ketamine (20 mg/kg), and atropine (0.02-0.05 mg/kg). The animal was then administered propofol (2 mg/kg) intravenously and endotracheal intubation was performed. Anesthesia was maintained using 1-3.5% inhaled isoflurane for the duration of the procedure. In order to induce IVD degeneration, a single annular injury was performed, as it was found the most reliable and reproducible method compared to nucleus aspiration or injection of apoptotic agents (K. S. Kim, S. T. Yoon, J. Li, J. S. Park, W. C. Hutton, Disc degeneration in the rabbit: a biochemical and radiological comparison between four disc injury models. *Spine (Phila Pa. 1976)* 30, 33-37 (2005)). Under fluoroscopic guidance, a 14 G Verteport needle (Stryker, Kalamazoo, Mich.) was used to penetrate and injure the annulus fibrosus of the IVD parallel to the endplate via a posterolateral approach. This procedure was repeated at four target levels: L1/L2, L2/L3, L3/L4 and L4/L5.

In Vivo MRI

Imaging experiments were performed on a 3 T clinical scanner (Magnetom Verio; Siemens Healthcare, Erlangen, Germany). Animals were placed in the right decubitus position with body array coils centered on the posterior aspect spinous process. Throughout the imaging procedures, anesthesia was maintained with isoflurane (1%-3.5%).

CEST MRI was performed using a two-dimensional reduced field of view TSE CEST sequence (TR/TE 1/4 10,500/10 ms, two averages, single shot). For each IVD, images were acquired in the axial plane with a slice thickness of 3 mm, field of view of 140×40 mm$^2$, and spatial resolution of 1.1×1.1 mm$^2$. CEST saturation module consists of 39 Gaussian-shaped pulses, with a duration $t_p$=80 ms for each pulse and an interpulse delay $t_d$=80 ms (duty cycle=50%, total saturation duration $T_s$=6240 ms) at saturation flip angle 900, 1500, 2100, and 3000 [$B_1$ amplitudes=flip angle/(g$t_p$)=0.73, 1.22, 1.71, and 2.45 µT; Z-spectrum was acquired with 10 different saturation frequencies at ±1.6, ±1.3, ±1.0, ±0.7, and ±0.4 ppm. The scan time of the CEST experiment for each IVD was approximately 40 min. The $B_0$ field was corrected using a water saturation shift referencing (WASSR) map.

$T_1$ mapping was performed using an inversion recovery TSE sequence with seven varying TI (50, 150, 350, 700, 1050, 1400, and 2000 ms). Other imaging parameters are: TR/TE=6000/12 ms; FOV=280×280 mm$^2$; spatial resolution=1.1×1.1×3 mm$^3$.

$T_2$ mapping was performed using a TSE sequence with varying echo delays (TE=12, 25, 50, 99, 199 and 397 ms; TR=6000 ms). Other imaging parameters are: TR=6000 ms; FOV=280×280 mm$^2$; spatial resolution=1.1×1.1×3 mm$^3$.

$T_{1\rho}$ mapping was performed using a rFOV TSE sequence with varying spin lock times (TSL=0, 10, 40 and 80 ms). The spin-lock frequency is 300 Hz. Other imaging parameters are: TR/TE=3500/9.1 ms; 1 average; FOV=140×40 mm$^2$; spatial resolution=1.1×1.1×3 mm$^3$). Imaging data analysis was performed with custom-written programs in MATLAB (MathWorks, Natick, Mass., USA).

IVD pH Measurement

Measurements of the pH inside the IVD were done immediately following animals' sacrifice. The spine was surgically exposed and a custom-made needle-shaped tissue pH probe (Warner Instruments, Hamden, Conn., USA) was inserted to the nucleus pulposus of the injured IVDs through a fine-cut incision of the annulus fibrosus.

Gene Expression Analysis

A quantitative RT-PCR was conducted on degenerated IVDs harvested at 2, 6 and 10 weeks after degeneration. The expression of genes from degenerative IVDs was compared to healthy IVDs harvested from each time point. Total RNA was extracted from the annulus fibrosus and the nucleus pulposus by using RNeasy Mini kit (Qiagen GmbH, Hilden, Germany) according to the manufacturer's protocol. RNA was retrotranscribed using random primers and reverse transcriptase (Promega Corp., Madison, Wis., USA). Quantitative real-time PCR was performed with the aid of ABI 7500 Prism system (Applied Biosystems, Foster City, Calif.). The porcine genes studied were Bradykinin receptor B1 (BDKRB1; Ss03389804_s1, Thermofisher scientific), calcitonin gene-related peptide (CGRP; Ss03386432_uH) and catechol-0-methyltransferase (COMT; Ss04247881_g1) to detect pain marker upregulation, interleukin-6 (IL-6; Ss03384604_u1) to examine the inflammatory response and brain-derived neurotrophic factor (BDNF; Ss03822335_s1) to determine nerve growth. 18 s was used as a housekeeping gene control.

Histological Analysis and Immunofluorescence Imaging

Histological analysis was performed on degenerated IVDs harvested at 2, 6 and 10 weeks after degeneration. The IVDs were sectioned and stained using hematoxylin and eosin for morphological analysis, as previously described (D. Sheyn, D. Cohn Yakubovich, I. Kallai, S. Su, X. Da, G. Pelled, W. Tawackoli, G. Cook-Weins, E. M. Schwarz, D. Gazit, Z. Gazit, PTH promotes allograft integration in a calvarial bone defect. *Mol Pharm* 10, 4462-4471 (2013). For immunofluorescent staining, tissues were deparaffinized, and the antigens were retrieved by incubation in preheated Target Retrieval Solution (Dako, Carpinteria, Calif.) for 45 minutes in 37° C. Nonspecific antigens were blocked by applying blocking serum-free solution (Dako). Slides were stained with primary antibodies against BDKRB1, CGRP, COMT, IL-6 and BDNF. The primary antibodies were applied to the slides and incubated in 4° C. overnight, washed off using PBS, and the slides were incubated with secondary antibodies for 1 hour in room temperature, after which they were washed off with PBS (Table S1). Slides were then stained with 4',6-diamidino-2-phenylindole dihydrochloride (1 µg/ml) for 5 minutes in the dark, after which they were again washed three times with PBS. A Vecta- Mount mounting medium (Vector Laboratories, Burlingame, Calif.) was applied to the tissue. The slides were imaged using a four-channel Laser Scanning Microscope 780 (Zeiss, Pleasanton, Calif.) with ×20 magnification, z-stacking, and 5×5 tile scanning. For zoom-in images, a single z-stacked image was generated. All samples were scanned using the same gain and exposure settings.

Statistical Analysis

GraphPad Prism 5.0f software (GraphPad Prism, San Diego, Calif.) was used to analyze the data. Data analysis was conducted using one-way or two-way ANOVA with Tukey's multiple comparison post hoc test. Results are presented as means ±SE. In box-and-whisker diagrams, the median is shown with a horizontal line, the box extends from the 25th to the 75th percentile, and the whiskers extend from the smallest value up to the largest. Pearson correlation was performed between qCEST and pH values. ROC curves were generated for qCEST and area under the curve was calculated. P values that were less than 0.05 were considered to be statistically significant.

TABLE S1

Antibodies used for immunofluorescence throughout the study.

| Antigen | 1' antibody | 2' antibody* |
| --- | --- | --- |
| BDKRB1 | Anti-BDKRB1 antibody TA317572 (OriGene Technologies Inc.), 1:100. | Donkey Anti-Rabbit Alexa Fluor 488 AffiniPure (cat# 711-545-152), 1:1,000. |
| BDNF | Anti-BDNF antibody MBS2002795 (MyBioSource), 1:100. | |
| COMT | Anti-COMT antibody LS-B4343 (LifeSpan Biosciences Inc.), 1:200. | Donkey Anti-Goat IgG (H + L) Alexa Flour 647 (cat# 705-605-003), 1:1,000. |
| IL-6 | Anti-IL6 antibody MAB686 (R&D Systems), 1:50. | Donkey Anti-Mouse IgG (H + L) ML Rhodamine-TRITC (cat# 715-025-150), 1:1,000. |
| CGRP | Anti-CGRP antibody ab81887 (Abcam), 1:200. | |

*Purchased from Jackson Immuno Research Laboratories Inc.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A method for detecting a condition in a subject, comprising:
   performing a scan of a region of the subject's body using a magnetic resonance imaging (MRI) scanner;
   generating an image of the region of the subject's body from the performed scan using a quantitative chemical exchange saturation transfer (qCEST) sequence;
   processing the image to detect one or more physiological biomarkers within the image of the region,
   wherein the physiological biomarkers comprise a labile proton exchange rate ($k_{sw}$) between a solute pool and a water pool; and
   determining that the subject has the condition if the labile proton exchange rate is increased relative to a reference value,
   wherein the increased labile proton exchange rate is greater than 200 exchanges/second.

2. The method of claim 1, wherein the increased labile proton exchange rate is correlated to a low pH value.

3. . The method of claim 2, wherein the low pH value is from 5.6 to 6.99.

4. The method of claim 2, wherein the low pH value is indicative of the subject having the condition.

5. The method of claim 1, wherein the increased labile proton exchange rate is from 201 to 1000 exchanges/second.

6. The method of claim 1, wherein the reference value is a reference labile proton exchange rate, wherein the reference labile proton exchange rate is from 100 to 200 exchanges/second.

7. The method of claim 6, wherein the reference labile proton exchange rate is correlated to a reference pH value.

8. The method of claim 7, wherein the reference pH value is from 7.0 to 7. 2.

9. The method of claim 1, wherein the condition is intervertebral disc degeneration, discogenic pain, discogenic low back pain, chronic low back pain, low back pain, back pain, chronic back pain, progressive intervertebral disc degeneration, osteoarthritis, rheumatoid arthritis, an articular cartilage injury, or temporomandibular disc degeneration, or combinations thereof.

10. The method of claim 1, wherein the region of the subject's body comprises a joint or an intervertebral disc.

11. The method of claim 1, wherein the condition is a painful condition.

12. The method of claim 1, wherein the increased labile proton exchange rate is correlated with an upregulation of one or more pain-related factors in the subject.

13. The method of claim 12, wherein the one or more pain-related factors are bradykinin receptor B1 (BDKRB1), calcitonin gene-related peptide (CGRP), or catechol-O-methyltransferase (COMT).

14. The method of claim 1, wherein the increased labile proton exchange rate is correlated with an upregulation of one or more inflammation-related factors in the subject.

15. The method of claim 14, wherein the inflammation-related factor is interleukin-6 (IL-6).

16. The method of claim 1, wherein the increased labile proton exchange rate is correlated with an upregulation of one or more neurogenic factors in the subject.

17. The method of claim 16, wherein the neurogenic factor is brain-derived neurotrophic factor (BDNF) or nerve growth factor (NGF).

18. The method of claim 1, wherein the quantitative chemical exchange saturation transfer (qCEST) sequence is a two dimension (2D) quantitative chemical exchange saturation transfer (qCEST) sequence, or a three dimension (3D) quantitative chemical exchange saturation transfer (qCEST) sequence.

19. The method of claim 1, wherein the MRI scanner is a 1.5 T MRI scanner, a 3.0 T MRI scanner, or a 7.0 T MRI scanner.

20. The method of claim 1, further comprising determining that an origin of the subject's condition is within the region of the subject's body where the physiological biomarker was measured.

21. The method of claim 1, further comprising selecting one or more treatments for the subject if the condition is determined.

22. A method for prognosing a condition associated with tissue degeneration and/or pain in a subject, comprising:
   performing a scan of a region of the subject's body using a magnetic resonance imaging (MRI) scanner;
   generating an image of the region of the subject's body from the performed scan using a quantitative chemical exchange saturation transfer (qCEST) sequence;
   processing the image to detect one or more physiological biomarkers within the image of the region,
   wherein the physiological biomarkers comprise a labile proton exchange rate ($k_{sw}$) between a solute pool and a water pool; and
   prognosing the condition by comparing a measurement of one or more physiological biomarkers to a previous measurement of the same one or more physiological biomarkers, wherein an increase in the labile proton exchange rate over time is a poor prognosis of the condition, wherein the increased labile proton exchange rate is greater than 200 exchanges/second.

23. A method for determining the risk of developing a condition in a subject, comprising:
   performing a scan of a region of the subject's body using a magnetic resonance imaging (MRI) scanner;
   generating an image of the region of the subject's body from the performed scan using a quantitative chemical exchange saturation transfer (qCEST) sequence;
   processing the image to detect one or more physiological biomarkers within the image of the region,
   wherein the physiological biomarkers comprise a labile proton exchange rate ($k_{sw}$) between a solute pool and a water pool; and
   comparing the labile proton exchange rate from the subject to a reference value, wherein an increase in the labile proton exchange rate from the subject compared to the reference value is indicative of an increased risk of the subject developing the condition, wherein the increased labile proton exchange rate is greater than 200 exchanges/second.

24. The method of claim 23, wherein the condition is intervertebral disc degeneration, discogenic pain, discogenic low back pain, chronic low back pain, low back pain, back pain, chronic back pain, progressive intervertebral disc degeneration, osteoarthritis, rheumatoid arthritis, an articular cartilage injury, or temporomandibular disc degeneration, or combinations thereof.

\* \* \* \* \*